United States Patent [19]
Blumenfeld et al.

[11] Patent Number: 5,998,133
[45] Date of Patent: *Dec. 7, 1999

[54] USE OF GENETIC MARKERS TO DIAGNOSE FAMILIAL DYSAUTONOMIA

[75] Inventors: Anat Blumenfeld, Mevaseret Zion, Israel; James F. Gusella, Framingham, Mass.; Xandra O. Breakefield, Newton, Mass.; Susan Slaugenhaupt, Quincy, Mass.

[73] Assignee: The General Hospital Corporation, Boston, Mass.

[*] Notice: This patent is subject to a terminal disclaimer.

[21] Appl. No.: 08/480,655

[22] Filed: Jun. 7, 1995

Related U.S. Application Data

[63] Continuation-in-part of application No. 08/049,678, Apr. 16, 1993, abandoned, which is a continuation-in-part of application No. 07/890,719, May 29, 1992, Pat. No. 5,387,506.

[51] Int. Cl.$^6$ ............................. C12Q 1/68; C07H 21/04; C12P 19/34
[52] U.S. Cl. ......................... 435/6; 435/91.2; 536/23.5; 536/24.31; 536/24.33
[58] Field of Search .................... 435/6, 91.2; 536/23.5, 536/24.33, 24.31; 436/63; 935/8, 9, 10, 17, 77, 78

[56] References Cited

PUBLICATIONS

Proceedings of the 8th International Congress of Human Genetics, Washington, D.C., USA, Oct. 6–11, 1991. Am J Hum Genet 49 (4 Suppl.) 1991. 336. Coden AJHGAG ISSN: 0002–9297 6—(C) File Biosis, Blumenfeld A. et al., *Advances in Linkage Analysis in Familial Dysautonomia*.
Blumenfeld A. et al. *Linkage Analysis in Familial Dysautonomia*, Bonne–Tamir, B. and A. Adam (Ed.) Genetic Diversity Among Jews: Disease and Markers of the DNA Level; Goodman's International Conference Israel, Jun. 1990. XXVIII+460P. Oxford University Press: New York, New York, USA; Oxford, England, UK. Illus. M.

J. Med Genet 30 (1). 1993. 47–52. Coden: Jmdgae ISSN: 0022–2593 2—(C) File Biosis Blumenfeld A et al. *Exculusion of Familial Dysautonomia from More than 60 Percent of the Genome*.

Kwaitkowski, et al., *Construction of a GT Polymorphism Map of Human 9q*, Genomics (1992), 12: 229–240.

Wilkie et al., *Linkage Map of Human chromosome 9 Microsatellite Polymorphisms*, Genomics (Feb. 1992) 12, 607–609.

Trotater et al., *Dinucleotide Repeat Polymorphism at the Debrisoquine 4–hydroxylase (CYP2D) Locus*, Nucleic Acid Research (1991) vol. 19, No. 10 p. 2802.

Browne et al., *Dincleotide Repeat Polymorphism at the DXS538 Locus*, Nucleic Acid Research (1991) vol. 19, No. 5 p. 1161.

(List continued on next page.)

*Primary Examiner*—Carla J. Myers
*Attorney, Agent, or Firm*—Morgan & Finnegan, L.L.P.

[57] ABSTRACT

Familial dysautonomia (FD), the Riley-Day syndrome, is an autosomal recessive disorder characterized by developmental loss of neurons from the sensory and autonomic nervous system. It is limited to the Ashkenazi Jewish population, where the carrier frequency is 1 in 30. We have mapped the FD gene to the chromosome region 9q31-q33 by linkage with ten DNA markers in twenty-six families. The maximum lod score of 21.1 with no recombinants was achieved with D9S58. This marker also showed strong linkage disequilibrium with FD, with one allele present on 73% of all affected chromosomes compared to 5.4% of control chromosomes ($X^2=3142$, 15 d.f. p<0.0001). The other nine markers, distributed within 23 cM proximal or distal to D9S58, also yielded significant linkage to FD. D9S53 and D9S105 represent the closest flanking markers for the disease gene. This localization will permit prenatal diagnosis of FD in affected families.

9 Claims, 6 Drawing Sheets

Lod Scores Between Dysautonomia and Chromosome 9 Markers

| Marker | Recombination Value | | | | | | | |
|---|---|---|---|---|---|---|---|---|
| | 0.00 | 0.05 | 0.10 | 0.20 | 0.30 | 0.40 | $\hat{\theta}$ | $\hat{z}$ |
| D9S15 | -∞ | -5.54 | -1.76 | 0.53 | 0.76 | 0.36 | 0.266 | 0.81 |
| D9S109 | -∞ | 5.54 | 5.42 | 3.85 | 2.04 | 0.60 | 0.066 | 5.62 |
| D9S29 | -∞ | 5.56 | 5.35 | 3.82 | 2.04 | 0.60 | 0.063 | 5.59 |
| D9S127 | -∞ | 8.01 | 7.21 | 4.82 | 2.44 | 0.68 | 0.040 | 8.05 |
| D9S58 | 18.48 | 15.93 | 13.39 | 8.47 | 4.22 | 1.23 | 0.000 | 18.48 |
| D9S59 | -∞ | 6.08 | 6.05 | 4.39 | 2.36 | 0.74 | 0.070 | 6.21 |
| HXB | -∞ | 5.99 | 5.89 | 4.27 | 2.30 | 0.70 | 0.068 | 5.91 |
| GSN | -∞ | 6.09 | 6.39 | 4.79 | 2.62 | 0.83 | 0.085 | 6.45 |
| ASS | -∞ | -5.07 | -1.64 | 0.41 | 0.55 | 0.20 | 0.303 | 0.56 |

OTHER PUBLICATIONS

Tsilfidis et al., *An SstI RFLP Detected by the Probe pKE2.1(D19S116) Localized to Human Chromosome 19q13.3,* Nucleic Acid Research (1991) vol. 19, No. 5, p. 1158.

Bowen et al., *AatlI Polymorphism in Von Wilebrand factor Gene at Codon 471,* Nucleic Acids Research, Vo. 19, No. 11 p. 3159.

Altherr et al., *A Highly Polymorphic VNTR Locus on the Long Arm of Chromosome 4,* Nucleic Acid Research (1991) vol. 19, No. 5, p. 1168.

M. Lathrop, et al. *Mapped set of Genetic Markers for Human Chromosome 9,* (1988), Academic Press, Inc., Genomics 3, pp. 361–366.

GDB Home, *Amplimer* —Name D9S310 Accession I.D. No. GDB 548985 (Apr. 1995).

S. Povey, et al. *Report on the Third International Workshop on Chromosome 9,* (1994) Ann. Am. Genet, 58:177–199.

GDB Home, *Amplimer* —Name D9S309, Accession I.D. No. GDB: 548966 (Apr. 1995).

C. Liebert, et al. *Identification of Simple Sequence Report 9SSR) Polymorphisms on Human Chromosome 9,* Second International Chromosome 9 Workshop, Apr. 17–20, 1993.

S. Slaugenhaupt et al., *Physical Mapping of the Familial Dysautonomia Gene Region of Human Chromosome 9,* Second International Chromosome 9 Workshop, Apr. 17–20, 1993.

M.A.Pericak–Vance, et al., *Report on the Fourth International Workshop on Chromosome 9,* Apr. 23–25, 1995.

Weissenbach, J. et al., *A Second Generation Linkage Map of the Human Genome,* (1992) Nature, 359:794–801.

Lod Scores Between Dysautonomia and Chromosome 9 Markers

| Marker | Recombination Value | | | | | | $\hat{\theta}$ | $\hat{Z}$ |
|---|---|---|---|---|---|---|---|---|
| | 0.00 | 0.05 | 0.10 | 0.20 | 0.30 | 0.40 | | |
| D9S15 | -∞ | -5.54 | -1.76 | 0.53 | 0.76 | 0.36 | 0.266 | 0.81 |
| D9S109 | -∞ | 5.54 | 5.42 | 3.85 | 2.04 | 0.60 | 0.066 | 5.62 |
| D9S29 | -∞ | 5.56 | 5.35 | 3.82 | 2.04 | 0.60 | 0.063 | 5.59 |
| D9S127 | -∞ | 8.01 | 7.21 | 4.82 | 2.44 | 0.68 | 0.040 | 8.05 |
| D9S58 | 18.48 | 15.93 | 13.39 | 8.47 | 4.22 | 1.23 | 0.000 | 18.48 |
| D9S59 | -∞ | 6.08 | 6.05 | 4.39 | 2.36 | 0.74 | 0.070 | 6.21 |
| HXB | -∞ | 5.99 | 5.89 | 4.27 | 2.30 | 0.70 | 0.068 | 5.91 |
| GSN | -∞ | 6.09 | 6.39 | 4.79 | 2.62 | 0.83 | 0.085 | 6.45 |
| ASS | -∞ | -5.07 | -1.64 | 0.41 | 0.55 | 0.20 | 0.303 | 0.56 |

FIG. 2

USE OF GENETIC MARKERS TO DIAGNOSE FAMILIAL DYSAUTONOMIA

This application is a continuation-in-part of U.S. patent application Ser. No. 08/049,678 filed Apr. 16, 1993 now abandoned, which is a continuation-in-part of U.S. patent application Ser. No. 07/890,719 issued as U.S. Pat. No. 5,387,506 filed May 29, 1992.

STATEMENT AS TO RIGHTS TO INVENTION

The present invention was developed at Massachusetts General Hospital under obligation to assign the invention to the same. The Dysautonomia Foundation has an option for an exclusive license for the present invention.

FIELD OF THE INVENTION

This invention relates to genetic testing; more specifically, to a method of detecting the presence of the familial dysautonomia gene and also the identification of the location of the familial dysautonomia gene in the genome.

BACKGROUND OF THE INVENTION

Familial dysautonomia, or the Riley-Day syndrome, is a rare inherited neurological disease affecting the development and survival of sensory, sympathetic and some parasympathetic neurons (Riley, C. M. et al., *Pediatrics* 1949; 3:468–477; Axelrod, F. B., et al., *Am. J. Dis. Child.* 1984; 138:947–954; Axelrod, F. B., *Cell. Molec. Biol. Neuronal Dev.* 1984; Ed.: Black, I. B., Plenum Press, NY; 331–340). It is the most common and the best known of a group of rare disorders, termed congenital sensory neuropathies, that are characterized by widespread sensory, and variable autonomic dysfunction. Patients with familial dysautonomia are affected from birth with a variety of symptoms such as decreased sensitivity to pain and temperature, vomiting crises and cardiovascular instability all of which might result from a deficiency in a neuronal growth factor pathway (Breakefield, X. O., et al., *Proc. Natl. Acad. Sci. USA* 1984; 81:4213–4216; Breakefield, X. O., et al., *Mol. Biol. Med.* 1986; 3:483–494). Neuropathological findings have clearly differentiated familial dysautonomia from other congenital sensory neuropathies (Axelrod, F. B., et al., *Am. J. Dis. Child.*, supra, Axelrod, F. B., *Cell. Molec. Biol. Neuronal Dev.*, supra.) The disorder is inherited as an autosomal recessive with complete penetrance and is currently confined to individuals of Ashkenazi Jewish descent (Brunt, P. W., et al., *Medicine* 1970; 49:343–374). In this population, the estimated carrier frequency is 1 in 30 with a disease incidence of 1 in 3600 births (Maayan, C., et al., *Clinical Genet.* 1987; 32:106–108). The clear-cut pattern of transmission, apparent restriction to one ethnic population and lack of confounding phenocopies suggest that all cases of familial dysautonomia might have descended from a single mutation (Axelrod, F. B., et al., *Am. J. Dis. Child.*, supra, Axelrod, F. B., *Cell. Molec. Biol. Neuronal Dev.*, supra).

For more than 40 years, familial dysautonomia related research concentrated on biochemical, physiological and histological-pathological aspects of the disorder. Although those studies contributed to a better understanding of the nature of the disease, and indicated that a deficiency in a neuronal growth factor pathway might be the cause of familial dysautonomia, they did not result in identification of the familial dysautonomia gene, thus, those studies did not contribute to the availability of a genetic test for familial dysautonomia.

Chromosomal localization of the gene causing familial dysautonomia can facilitate genetic counseling and prenatal diagnosis in affected families. Subsequent delineation of closely linked markers which show strong linkage disequilibrium with the disorder and ultimately, identification of the defective gene can allow screening of the entire at-risk population to identify carriers, and potentially reduce the incidence of new cases.

Linkage analysis can be used to find the location of a gene causing a hereditary disorder and does not require any knowledge of the biochemical nature of the disease, i.e. the mutated protein that is believed to cause the disease. Traditional approaches depend on assumptions concerning the disease process that might implicate a known protein as a candidate to be evaluated. The genetic localization approach using linkage analysis (positional cloning) can be used to first find the chromosomal region in which the defective gene is located and then to gradually reduce the size of the region in order to determine the location of the specific mutated gene as precisely as possible. After the gene itself is identified within the candidate region, the messenger RNA and the protein are identified and along with the DNA, are checked for mutations.

This latter approach has practical implications since the location of the gene can be used for prenatal diagnosis even before the altered gene that causes the disease is found. Identification of DNA markers linked to the disease gene will enable molecular diagnosis of carriers of the disease gene for familial dysautonomia and the determination of the probability of having the disease. This identification of the presence of the disease gene also enables persons to evaluate either genetic probability of passing this gene to their offspring or the presence of the mutated gene in an unborn child. The mutation(s) in the specific gene responsible for the pathogenesis of familial dysautonomia has its origin in the Ashkenazi Jewish population. Accordingly, individuals of Ashkenazi Jewish descent are at greatest risk of carrying the altered gene.

The transmission of a disease within families, then, can be used to find the defective gene. This approach to molecular etiology is especially useful in studies of inherited neurologic disorders, as only several thousands of the hundred-or-so thousand genes active in the nervous system are known, and nervous tissue is hard to obtain for biochemical analysis.

Linkage analysis is possible because of the nature of inheritance of chromosomes from parents to offspring. During meiosis the two homologues pair to guide their proper separation to daughter cells. While they are lined up and paired, the two homologues exchange pieces of the chromosomes, in an event called "crossing over" or "recombination". The resulting chromosomes are chimeric, that is, they contain parts that originate from both parental homologues. The closer together two sequences are on the chromosome, the less likely that a recombination event will occur between them, and the more closely linked they are. In a linkage analysis experiment, two positions on a chromosome are followed from one generation to the next to determine the frequency of recombination between them. In a study of an inherited disease, one of the chromosomal positions is marked by the disease gene or its normal counterpart, i.e. the inheritance of the chromosomal region can be determined by examining whether the individual displays symptoms of the disorder or is a parent of an affected individual (carrier) or not. The other position is marked by a DNA sequence that shows natural variation in the population such that the two homologues can be distinguished based on the copy of the "marker" sequence that they possess. In every family, the inheritance of the genetic marker sequence is compared to the inheritance of the disease state. If within a family carrying a recessive disorder such as familial dysautonomia every affected individual carries the same form of the marker and all the unaffected individuals carry at least one different form of the marker, there is a great probability that the disease gene and the marker are located close to each other. In this way, chromosomes may be systematically checked with known markers and compared to the disease state. The data obtained from the different families is combined, and analyzed together by a computer using statistical methods. The result is information indicating the probability of linkage between the genetic marker and the disease gene at different distance intervals. A positive result indicates that the disease is very close to the marker, while a negative result indicates that it is far away on that chromosome, or on an entirely different chromosome.

Linkage analysis is performed by typing all members of the affected family at a given marker locus and evaluating the co-inheritance of a particular disease gene with the marker probe, thereby determining whether the two of them are close to each other in the genome. The recombination frequency can be used as a measure of the genetic distance between two gene loci. A recombination frequency of 1% is equivalent to 1 map unit, or 1 centiMorgan (cM), which is roughly equivalent to 1,000 kb of DNA. This relationship holds up to frequencies of about 20% (or 20 cM).

The entire human genome is 3,300 cM long. In order to find an unknown disease gene within 5–10 CM of a marker locus, the whole human genome can be searched with 165–330 informative marker loci spaced at 5–10 cM intervals (Botstein, D. R. I., et al., *Am. J. Hum. Genet.* 1980; 32:314–331). The reliability of linkage results is established by using a number of statistical methods.

The method most commonly used for the analysis of linkage in humans is the LOD score method, developed by Morton, 1955; and incorporated into the computer program LIPED by Ott, 1976. LOD scores are the logarithm of the ratio of the likelihood that two loci are linked at a given distance to that they are not linked (>50 cM apart). The advantage of using logarithmic values is that they can be summed among families with the same disease. This becomes necessary given the relatively small size of human families.

By convention, a total lod score greater than +3.0 (that is, odds of linkage at the specified recombination frequency being 1000 times greater than odds of no linkage) is considered to be significant evidence for linkage at that particular recombination frequency; a total lod score of less than −2.0 (that is, odds of no linkage being 100 times greater than odds of linkage at the specified frequency) is considered to be strong evidence that the two loci under consideration are not linked at that particular recombination frequency.

Until recently, most linkage analyses have been performed on the basis of two-point data; that is, the relationship between the disorder under consideration and a particular genetic marker. However, as a result of the rapid advances in mapping the human genome over the last few years, and concomitant improvements in computer methodology, it has become feasible to carry out linkage analyses using multi-point data; that is, a simultaneous analysis of linkage between the disease and several linked genetic markers, when the recombination (genetic) distance among the markers is known.

Multi-point analysis is advantageous for two reasons. First, the informativeness of the pedigree is usually increased. Each pedigree has a certain amount of potential information, dependent on the number of parents heterozygous for the marker loci and the number of affected individuals in the family. However, not all markers are sufficiently polymorphic as to be informative in all those individuals. If multiple markers are considered simultaneously, then the probability of an individual being heterozygous for at least one of the markers is greatly increased. Second, and more important, an indication of the position of the disease gene among the markers may be determined. This may allow identification of flanking markers, and thus eventually allows isolation of a small region in which the disease gene resides. Lathrop, G. M., et al., *Proc. Natl. Acad. Sci. USA* 1984; 81:3443–3446 have written the most widely used computer package, LINKAGE, for multi-point analysis.

When two loci are extremely close together, recombination between them is very rare. In fact, the rate at which the two neighboring loci recombine can be so slow as to be unobservable except over many generations. The resulting allelic association is generally referred to as linkage disequilibrium. Linkage disequilibrium is defined as specific alleles at two loci that are observed together on a chromosome more often than expected from their frequencies in the population. Such results are strongly influenced by founder and subpopulation effects, so it is generally necessary to examine data only within one ethnic group or population isolate, which is the case for familial dysautonomia, which is only found in individuals of Ashkenazi Jewish descent. Linkage disequilibrium is usually used to further define the chromosomal region containing the disease gene, once linkage has been demonstrated in a specific region. When disequilibrium is suspected, the affected individuals are checked for increased frequency of specific alleles for the marker loci. An excess frequency of any allele, as measured against general population frequencies (using the Chi-square statistics) would indicate linkage disequilibrium. The major advantage of disequilibrium study over standard linkage analysis is the need to test only a single affected individual per family, which is the usual case with rare recessive disorders, thus increasing the population amenable for analysis.

The marker locus must be very tightly linked to the disease locus in order for linkage disequilibrium to exist. Potentially, markers within a few cM of the disease gene could be examined and no linkage disequilibrium detected. Linkage disequilibrium has been observed with markers within 500 kb of the cystic fibrosis gene (Kerem, et al., *Science* 1989; 245:1073–1080). If linkage is found with several marker loci that are spaced along several centiMorgans, and none of them show recombination between the marker tested and the disease status in affected families, disequilibrium is the only genetic approach that can narrow down the chromosomal region linked to the disease gene.

A specific DNA sequence in an individual can undergo many different changes, such as deletion of a sequence of DNA, insertion of a sequence that was duplicated, inversion of a sequence, or conversion of a single nucleotide to another. Changes in a specific DNA may be traced by using restriction enzymes that recognize specific DNA sequences of 4–6 nucleotides. Restriction enzymes, cut (digest) the DNA at their specific recognized sequence, resulting in one million or so pieces. When a difference exists that changes a sequence recognized by a restriction enzyme to one not recognized, the piece of DNA produced by cutting the region will be of a different size. The various possible fragment sizes from a given region therefore depend on the precise sequence of DNA in the region. Variation in the fragments produced is termed "restriction fragment length polymorphism" (RFLP). The different sized-fragments reflecting different variant DNA sequences can be visualized by separating the digested DNA according to its size on an agarose gel and visualizing the individual fragments by annealing to a radioactively labeled, DNA "probe". Each individual can carry two different forms of the specific sequence. When the two homologues carry the same form of the polymorphism, one band will be seen. More than two forms of a polymorphism may exist for a specific DNA marker in the population, but in one family just four forms are possible; two from each parent. Each child inherits one form of the polymorphism from each parent. Thus, the origin of each chromosome can be traced (maternal or paternal origin).

RFLPs have proven to be somewhat limiting in that they usually give only two alleles at a locus and not all parents are heterozygous for these alleles and thus informative for linkage. Newer methods take advantage of the presence of DNA sequences that are repeated in tandem, variable numbers of time and that are scattered throughout the human genome. The first of these described were variable number tandem repeats of core sequences (VNTRs) (Jeffreys, A. J. V., et al., Nature 1985; 314:67–73; Nakamura, Y. M., et al., Science 1987; 235:1616–1622). VNTRs are detected using unique sequences of DNA adjacent to the tandem repeat as marker probes, and digesting the DNA with restriction enzymes that do not recognize sites within the core sequence. However, highly informative VNTR loci have not been found on all chromosome arms, and those which have been identified are often situated near telomeres (Royle, et al., Genomics 1988; 3:352–360), leaving large regions of the genome out of reach of these multiallelic marker loci.

Recently, it was discovered that eukaryotic DNA has tandem repeats of very short simple sequences termed SSRs (Simple Sequence Repeat polymorphisms) such as $(dC-dA)_n$ $(dG-dT)_n$ where n=10–60 (termed GT repeat). The (dG-dT) repeats occur every 30–60 kb along the genome (Weber, J. L., et al., Am. J. Hum. Genet., 1989; 44:388–396; Litt, M., et al. Am. J. Hum. Genet., 1989; 44:397–401), and Alu 3' (A)n repeats occur approximately every 5 kb (Economou, Proc. Natl. Acad. Sci. U.S.A. 1990; 87:2951–4). Other repeats, such as GA repeats, trinucleotide and tetranucleotide repeats are less common.

Oligonucleotides encoding flanking regions of these repeats are used as primers for the polymerase chain reaction (PCR) (Saiki, Science 1988; 239:484–491) on a small sample of DNA. By amplifying the DNA with radioactive nucleotides, the sample may be quickly resolved on a sequencing gel and visualized by autoradiography. Because these polymorphisms are comprised of alleles differing in length by only a few base pairs, they are not detectable by conventional Southern blotting as used in traditional RFLP analysis.

The use of PCR to characterize SSRs such as GT polymorphic markers enables the use of less DNA, typically only ten nanograms of genomic DNA is needed, and is faster than standard RFLP analysis, because it essentially only involves amplification and electrophoresis (Weber, supra).

Consequently, the present invention comprises genetic linkage analysis to identify an individual having the familial dysautonomia gene. In addition, discovery of markers linked to the familial dysautonomia gene will enable researchers to focus future analysis on a small chromosomal region and will accelerate the identification and sequencing of the familial dysautonomia gene.

It is an object of the present invention to locate markers linked to the familial dysautonomia gene and to identify the location of the familial dysautonomia gene in the human genome.

It is a further object of the present invention to provide a genetic test specific for the familial dysautonomia gene by analysis of DNA markers linked to the familial dysautonomia gene.

It is a still further object of the present invention to provide a genetic test for the prenatal diagnosis and carrier detection specific for the familial dysautonomia gene by analysis of DNA markers linked to the familial dysautonomia gene. it is yet another object of this invention to provide nucleic acid sequences encoding primers useful for detecting polymorphisms or markers linked to the familial dysautonomia gene.

It is a further object of the present invention to isolate and characterize the gene for familial dysautonomia by analysis of DNA markers linked to the familial dysautonomia gene.

It is also an object of this invention to provide products useful for carrying out the assay in individuals from affected familial dysautonomia families, such as DNA probes, kits and the like.

SUMMARY OF THE INVENTION

The present invention describes, for the first time, the chromosomal location which carries the gene responsible for familial dysautonomia and provides a method of detecting the presence of a familial dysautonomia gene in a subject. The location by applicants of the familial dysautonomia gene is on the long arm of human chromosome 9 (q arm) more specifically between D9S59 and D9S127. In addition, we have mapped the FD gene to the chromosome region 9q31-q33. Within the chromosomal region defined by D9S59 and D9S127, the closest flanking markers for the disease gene are D9S105, and D9S172. Other markers encompassed by this region include D9S53, D9S310, D9S309 AND D9S174. A most probable location of the familial dysautonomia gene is close to D9S58.

Linkage analysis with markers located on the long arm of human chromosome 9 is used to identify the inheritance of the allele causing familial dysautonomia with 80–90% accuracy, or greater, at the present time.

In particular, the test is carried out by studying the heritability of a combination of two or more polymorphisms linked to familial dysautonomia among any number of suitable family members so as to allow the determination of phenotype. The test can be used prenatally to screen a fetus or presymptomatically, to screen a subject at risk through his/her family.

The invention also extends to products useful for carrying out the assay, such as DNA probes (labelled or unlabelled), kits and the like.

BRIEF DESCRIPTION OF THE DRAWINGS

FIG. 2—Table of lod scores of different chromosome 9 markers in dysautonomia families. The lod scores were calculated assuming conventional recombination values (θ) between familial dysautonomia and the marker; 0, 0.05, 0.1, 0.2, 0.3, 0.4. When there is at least one recombination event between a marker tested and the disease, the lod score at θ=0 is minus infinity. At other recombination values, lod scores can be positive or negative. The highest lod score obtained by each marker ($\hat{Z}$), and the recombination value in which that lod score was calculated ($\hat{\theta}$), are also included. This gives a rough estimation of the genetic distance between the marker and the disease. The markers are ordered according to their location on chromosome 9, when D9S15 is the most centromeric one, and ASS is the closest to the telomere. In some cases, the order of the markers is unknown, because they were not placed on the same genetic map and were not typed with the same pedigrees (D9S109-D9S29-D9S127). In this case the order was determined according to $\hat{\theta}$ and according to recombination events that were detected while setting the phase (maternal or paternal origin) of the chromosones in FD families. Additional data from other markers is also presented in Table 2.

Physical map of human chromosome 9 markers. The names of the bands on chromosome 9 were determined according to Giemsa dyes. All the markers that show linkage with familial dysautonomia (FIG. 2) are located on the long arm (q arm) of chromosome 9, most of which are on band 31.

The genetic map positions of those FD-linked markers whose relative order was supported by odds of greater than 1000:1 was determined from combining the CEPH panel and the Venezuelan reference pedigree. The relative order of D9S109 and D9S127 could not be determined. D9S29 could not be positioned, but data from the FD families suggest that it maps as shown.

Figure 4A:
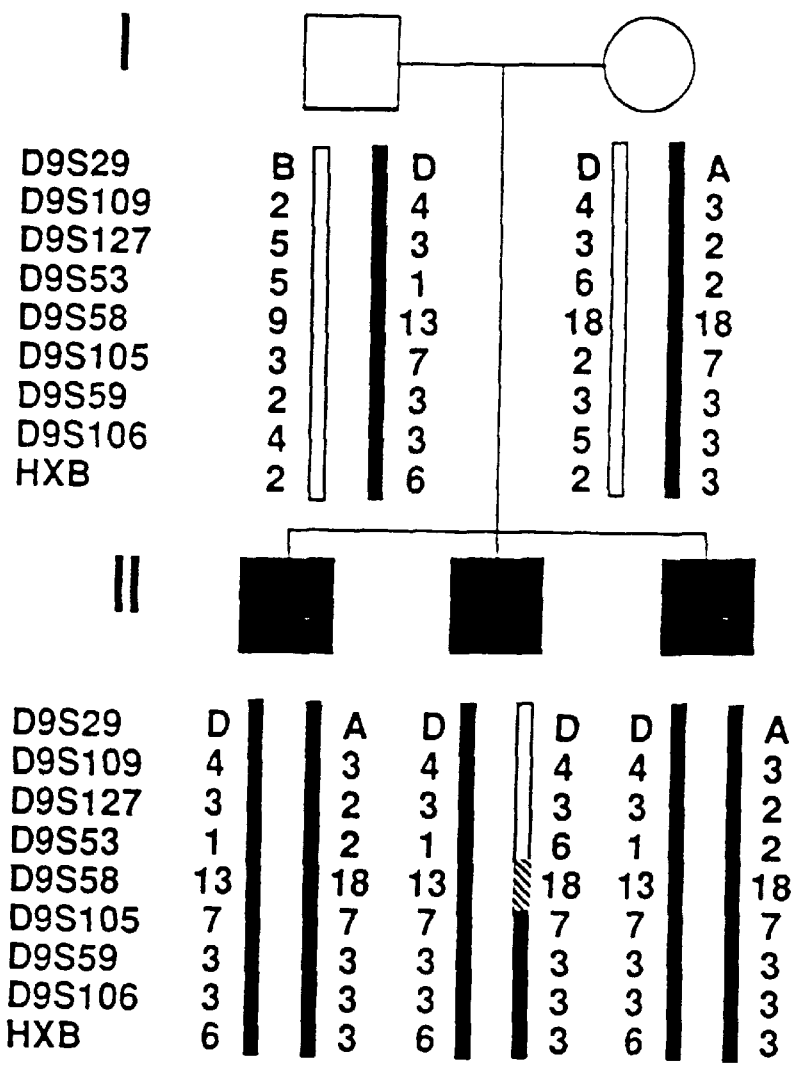
Figure 4B:
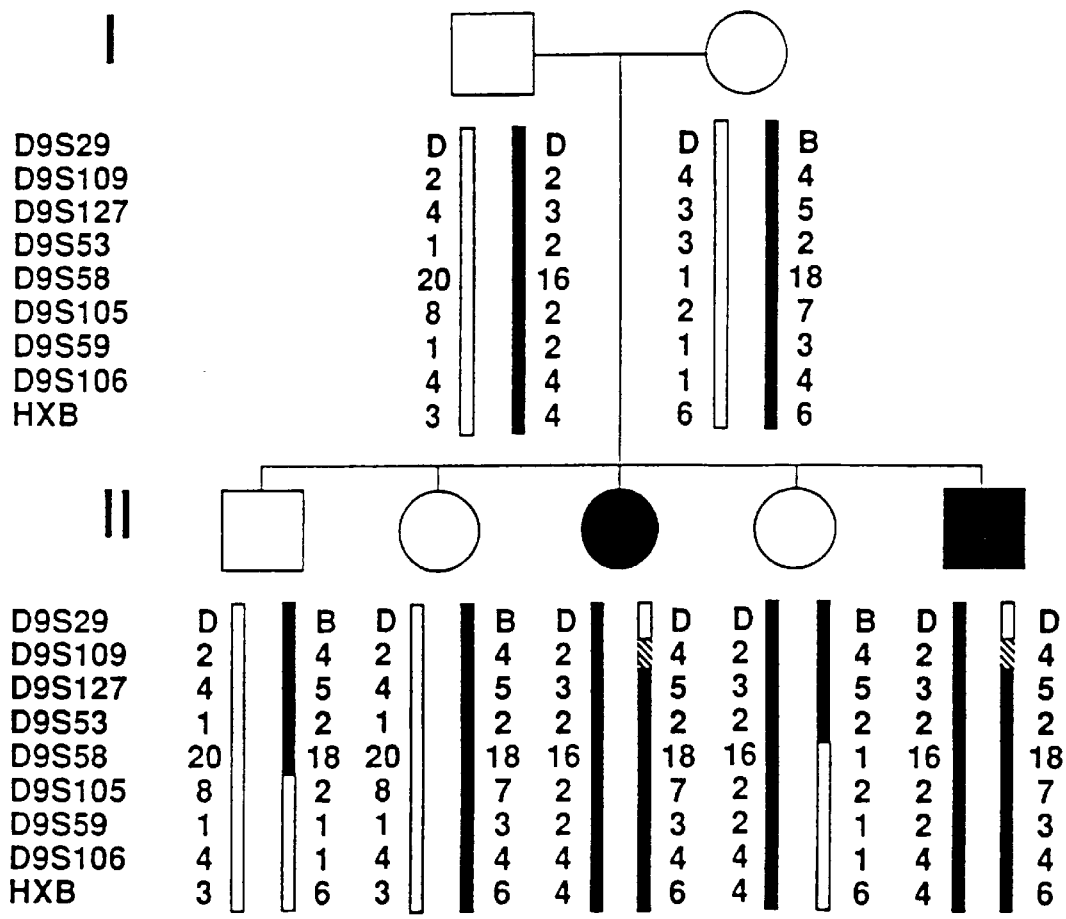

FIGS. 4A and 4B—Examples of recombination events localizing FD.

The region cosegregating with FD is shown as a filled box in two nuclear families (FIG. 4A: pedigree 21; FIG. 4B: pedigree 17). Hatched boxes indicate uncertainty with respect to the precise position of a crossover due to uniformativeness of D9S58 in the mother of pedigree 21, and D9S109 in the mother of pedigree 17. The recombination event in pedigree 21 is the only instance of all 26 FD families where a crossover occurred within the D9S53-D9S105 interval that could not be placed relative to D9S58.

Figure 5:
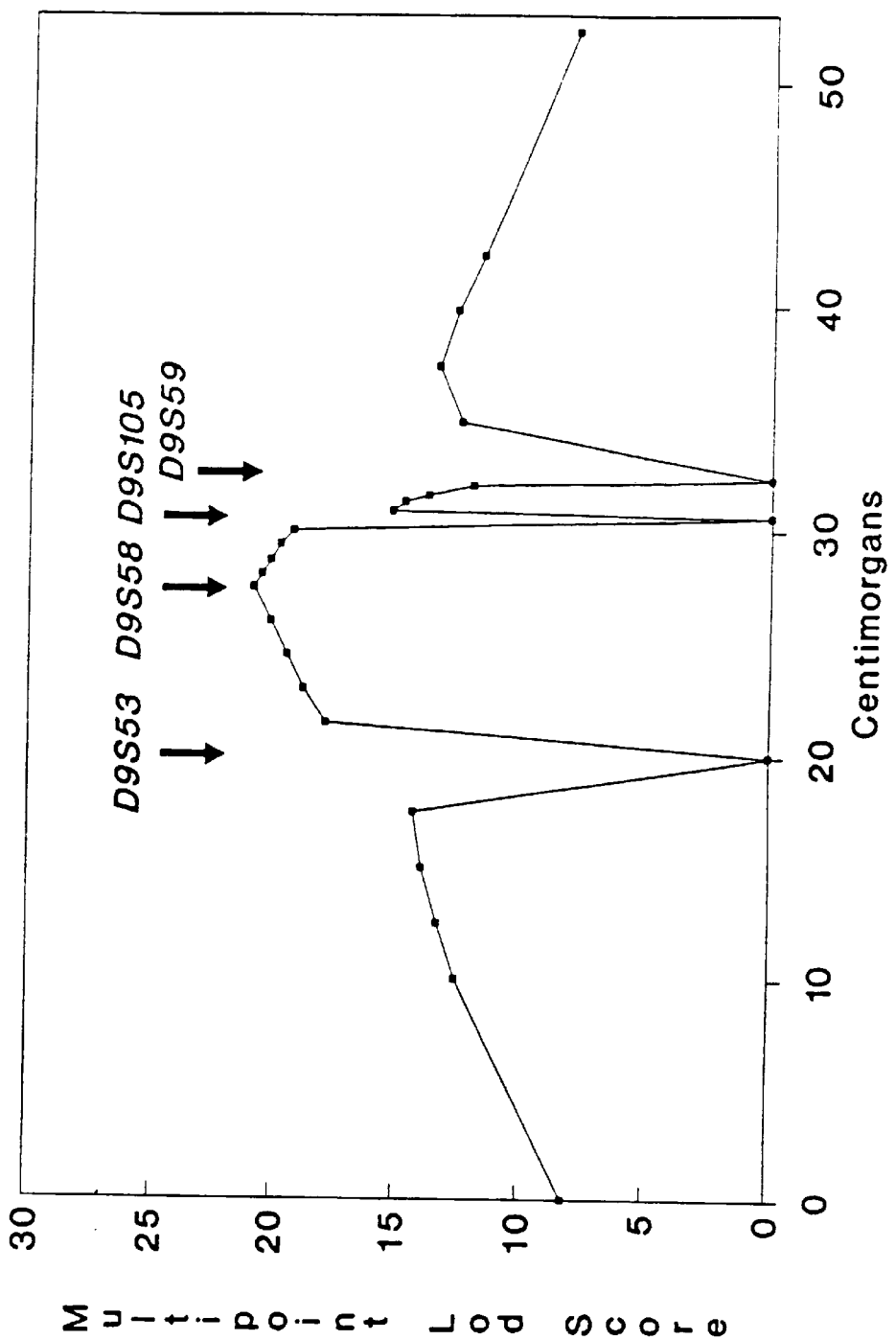

FIG. 5—Multipoint linkage of FD to chromosome 9.

FD was mapped with respect to the following map generated from the Venezuelan reference pedigree:

D9S53-7.5cM -D9S58-3.1cM -D9S105 1.7cM-D9S59
Arrows denote the map location of each marker locus.

DESCRIPTION OF THE PREFERRED EMBODIMENTS

The present invention further describes, for the first time, the location and chromosomal band which carries the gene responsible for familial dysautonomia.

Figure 1:
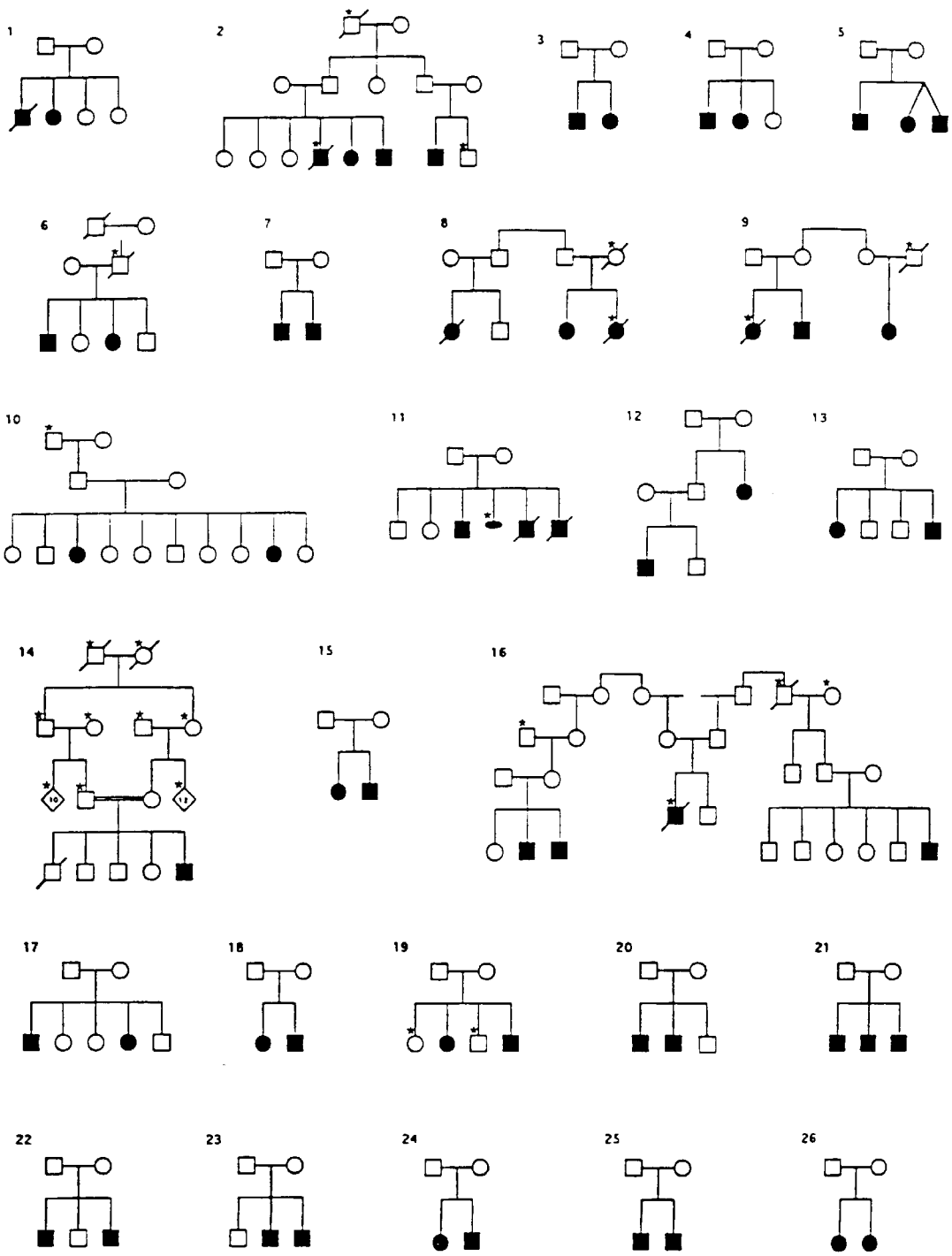
FIG. 1—Pedigrees of twenty-six families affected with familial dysautonomia that were used for linkage analysis. Symbols: empty circle unaffected female; filled circle, affected female; empty square, unaffected male; filled square, affected male; slashed symbol, deceased; star symbol, blood not collected.

To find the chromosomal location of the familial dysautonomia gene, polymorphic markers were typed in 26 families (FIG. 1). All selected families have two or three dysautonomic members (25 families), or consanguinity between the parents (one family). Thirty other families with one surviving FD member and 125 patients whose parents were not collected were used for allelic association studies. All families were collected in North America or Israel. The diagnosis of FD was confirmed in all cases based on standard criteria (Axelrod, F. B. & Pearson, J., *Am. J. Dis.* *Child.* 1984; 138:947–954; Axelrod, F. B., *Cell. and Molec. Biol. of Neuronal Dev.* 1984; Ed: Black IB Plenum Press, NY 331–340). DNAs from all family members, carriers, affected and unaffected, were tested with each marker. The result of the typing was compared to the disease status of each individual. Linkage analysis computer data management and statistical programs were employed and the lod scores of the different families were pooled together to give the lod score for each marker at different distances from the disease.

Control individuals were unrelated members of Ashkenazi Jewish families with idiopathic torsion dystonia (n=130, 260 chromosomes) who manifested no dystonic or dysautonomic symptoms. The torsion dystonia gene (DYTI) was mapped to 9q34 (Kramer, P. L. et al.,*Ann. Neurol.* 1990; 27:114–120); and is tightly linked to ABL and ASS, (Ozelius, L. J. et al.,*Am. J. Hum. Genet* 1992; 50:619–628); both of which were excluded for linkage with FD (Table 2). Unaffected chromosomes from the FD parents (110 chromosomes) were not used in the linkage disequilibrium studies; however, they yielded allele frequencies similar to the other control population.

Over 250 DNA polymorphisms distributed on all 22 autosomes were checked before linkage was found. Most of the polymorphisms yielded negative lod scores values and, hence, allowed the exclusion of chromosomal regions as possible sites for the familial dysautonomia gene. The few that had positive lod scores at some distances from the markers, were slightly positive but far from +3.0, that is conventionally accepted as a minimal demand for linkage. Moreover, those slightly positive markers were surrounded by negative flanking markers, indicating that the familial dysautonomia gene was not in the immediate vicinity of that chromosomal region.

The present invention relates to the location of polymorphic markers on the long arm of human chromosome 9, which are linked to the familial dysautonomia gene and enables linkage analysis to predict both an affected individual having both familial dysautonomia genes and a carrier with only one familial dysautonomia gene. Linkage analysis with these polymorphisms can identify the inheritance of the familial dysautonomia allele with at least 80–90% accuracy. Polymorphisms are DNA sequences located on the long arm of human chromosome 9. More specifically those polymorphisms are in, or immediately adjacent to the q31 band on the long arm of chromosome 9. Even more specifically, the familial dysautonomia gene is mapped to the chromosome region 9q31-q33 by linkage with ten DNA markers in twenty-six families. The linkage analysis of the invention can be carried out by using any polymorphism linked to the familial dysautonomia allele. The use of the term polymorphism is intended to encompass any marker DNA sequence which is linked to the familial dysautonomia gene. The polymorphism can be a polymorphic repeating sequence or allelic forms of a gene. The polymorphism must be located close to, or be the same as, the familial dysautonomia gene. If located close to the familial dysautonomia gene, the polymorphism must be sufficiently close to the familial dysautonomia gene such that the familial dysautonomia gene and the marker are linked. Linkage may be determined by a significant lod score or other acceptable statistical linkage determination.

The marker can be detected by a variety of methods. The preferred detection means uses radioactive nucleotides in PCR amplification of the polymorphism, or randomly labeled probes in hybridization reactions. Other detection methods such as the ligase chain reaction (LCR) can also be used. The polymorphism can be detectably labeled by a radioisotope or by chemical modification enabling direct detection of the polymorphism. Fluorescent or calorimetric means can also be used. Detection of the polymorphism can be indirect, e.g. a radioactive complementary strand of DNA, resulting from incorporation of radioactive nucleotides in a polymerase chain reaction.

For typing restriction fragment length polymorphisms (RFLPs) and VNTR polymorphisms, genomic DNA prepared from cell lines derived from all members of families affected with familial dysautonomia was digested with restriction endonuclease, resolved by electrophoresis on 0.8% agarose gels and transferred to Hybond N+ membranes. Genomic DNA was either prepared form cell lines using the SDS-proteinase K method, (Blumenfeld, A. et al., *J. Med. Genet.* 1993; 30:47–52) or directly from blood using the Chelex method (Walsh, P. S. et al., *BioTech.* 1991; 10:506–513). Blots were hybridized with probe DNAs radioactively labeled by random priming and visualized by autoradiography (Ozelius, L., et al., *Neuron* 1989; 2:1427–1434).

For typing simple sequence repeat polymorphisms, the method described by Weber, *Am. J. Hum. Genet., supra*, was used with the following modifications; PCR reaction volume was reduced to 10 μl using 5–10 ng genomic DNA, 40 ng of each primer, and about 0.25 U Taq polymerase (Boehringer). In most cases α-$^{32}$P-dGTP (3,000 Ci/mmole, Amersham) was used as the labelled nucleotide. PCR conditions varied as has been previously described for the specific markers. Dried gels were subjected to autoradiography for 4–16 hours using Kodak X-OMAT AR film.

The following markers were used: D9S7 (Ozelius, L. J. et al., *Genomics* 1992; 14:715–720; NIH/CEPH Collaborative Mapping Group, Science 1992; 258:67–86; Williamson, R. et al., *Cytogenet. Cell Genet.* 1991; 58:1190–1833), D9S15 (Kwiatkowski, D. J., et al., *Genomics* 1992; 12:229–240; Genome DataBase, Welch WH Medical Library, Baltimore, Md. 21205; Ozelius, L. J. et al., *Genomics* 1992; 14:715–720; NIH/CEPH Collaborative Mapping Group, *Science* 1992; 258, 67–86), D9S29 (Ozelius, L. J. et al., *Genomics* 1992; 14:715–720; Williamson, R. et al., *Cytogenet. Cell Genet.* 1991; 58:1190–1833), D9S53 (Genome Data Base, Welch WH Medical Library, Baltimore, Md. 21205; Ozelius, L. J. et al., *Genomics* 1992; 14:715–720; NIH/CEPH Collaborative Mapping Group, *Science* 1992; 258:67–86; Wilkie, P. J., et al., *Genomics* 1992; 12:607–609), D9S58 (Kwiatkowski, D. J. et al., *Genomics* 1992; 12:229–240; Ozelius, L. J. et al., *Genomics* 1992; 14:715–720; NIH/CEPH Collaborative Mapping Group, *Science* 1992; 258:67–86), D9S59 (Kwiatkowski, D. J. et al., *Genomics* 1992; 12:229–240; Ozelius, L. J. et al., *Genomics* 1992; 14:715–720), D9S66 (Kwiatkowski, D. J. et al., *Genomics* 1992; 12:229–240; Ozelius, L. J. et al., *Genomics* 1992; 14:715–720; NIH/CEPH Collaborative Mapping Group, *Science* 1992; 258:67–86), D9S105 (NIH/CEPH Collaborative Mapping Group, *Science* 1992; 258:67–86; Wilkie, P. J. et al., *Genomics* 1992; 12:607–609), D9S106 (Wilkie, P. J. et al., *Genomics* 1992; 12:607–609), D9S109 (NIH/CEPH Collaborative Mapping Group, *Science* 1992; 258:67–86; Furlong, R. A. et al., *Nucleic Acids Res.* 1992; 20:925), D9S127 (NIH/CEPH Collaborative Mapping Group, *Science* 1992; 258:67–86; Lyall, J. E. W. et al., *Nucleic Acids Res.* 1992; 20:925), HXB (Ozelius, L. J. et al., *Genomics* 1992; 14:715–720; NIH/CEPH Collaborative Mapping Group, *Science* 1992; 258:67–86; Ozelius, L., et al., *Hum. Molec. Genet.* 1992; 1:141; Povey, S. et al., *Ann. Hum. Genet.* 1992; 56:167–221), GSN (Ozelius, L. J. et al., *Genomics* 1992; 14:715–720; NIH/CEPH Collaborative Mapping Group, *Science* 1992; 258:67–86; Williamson, R. et al., *Cytogenet. Cell Genet.* 1991; 58:1190–1833), ABL (Kwiatkowski, D. J. et al., *Genomics* 1992; 12:229–240; Ozelius, L. J. et al., Genomics 1992; 14:715–720; NIH/ CEPH Collaborative Mapping Group, *Science* 1992; 258:67–86), and ASS (Kwiatkowski, D. J. et al., *Genomics* 1992; 12:229–240; Ozelius, L. J. et al., *Genomics* 1992; 14:715–720; NIH/CEPH Collaborative Mapping Group, *Science* 1992; 258:67–86).

The LIPIN (v. 2.1) data management program was used for entry of marker phenotypes into a VAX4500 computer. Pairwise lod scores were calculated using MLINK (v. 3.5) and LINKMAP (V.4.9) (Lathrop, G. M. et al. *Proc. Natl. Acad. Sci. USA* 1984; 81:3443–3446). For multipoint analysis, the loop in family 14 was broken, and only the portion of family 16 with two surviving affecteds was used. Consequently, the maximum multi-point lod score was slightly lower than the maximum two-point score with D9S58. Autosomal recessive inheritance, complete penetrance, no rate of new mutations, and a gene frequency of 1/60 were assumed for familial dysautonomia.

The relative order of most of the markers has been established previously in both the Venezuelan reference pedigree and in the CEPH panel (Kwiatkowski, D. J. et al. *Genomics* 1992; 12:229–240; Ozelius, L. J. et al., *Genomics* 1992; 14:715–720; NIH/CEPH Collaborative Mapping Group, *Science* 1992; 258:67–86; Wilkie, P. J. et al. *Genomics* 1992; 12:607–609; Povey, S. et al., *Ann. Hum. Genet.* 1992; 56:167–221). To obtain accurate map distances for the multi-point analysis, we genotyped D9S105 and D9S53 in the original 17 sibships of the Venezuelan reference pedigree (Tanzi, R. E. et al., *Genomics* 1988; 3:129–136. These data were analyzed in conjunction with previously typed markers (Kwiatkowski, D. J. et al., *Genomics* 1992; 12:229–240; Ozelius, L. J. et al., *Genomics* 1992; 14:715–720) using the MAPMAKER program (version 1.0) (Lander, E. S. et al., *Genomics* 1987; 1:174–181). For comparison, we genotyped the CEPH panel for D9S59 and reanalyzed the previously reported data, NIH/CEPH Collaborative Mapping Group, *Science* 1992; 258:67–86; Wilkie, P. J. et al., Genomics 1992; 12:607–609). The distances used in the multi-point analysis (FIG. 5) were derived from the Venezuelan data set after error checking of apparent double recombinants. In both reference pedigree sets, the marker order was identical and the distances between adjacent markers were similar.

Figure 3:
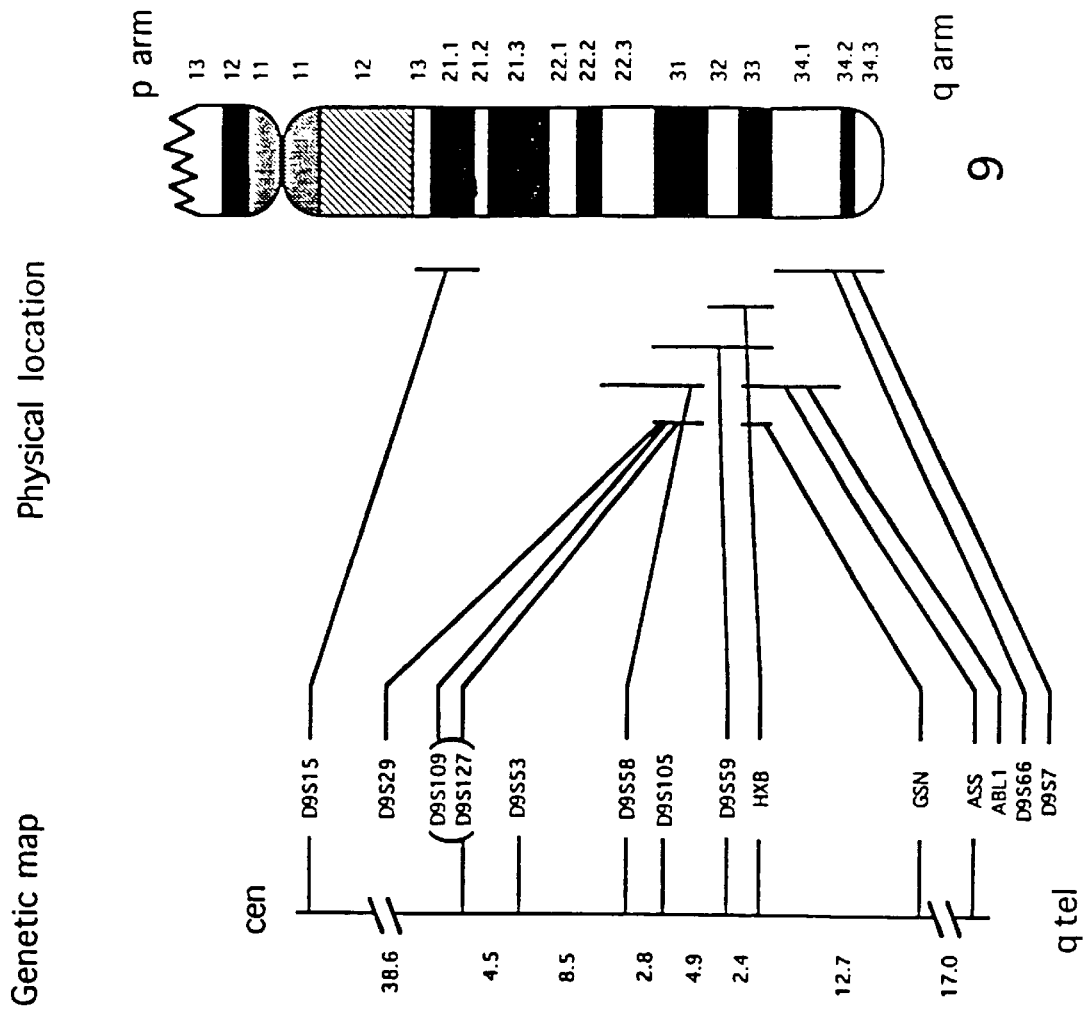
FIG. 3—Physical and genetic map of chromosome 9 markers.

The first DNA polymorphism that gave a significant positive lod score (FIG. 2) was HXB which is located on the long arm of chromosome 9 (FIG. 3). Table 1 provides the oligonucleotide primer sequences for each polymorphism and the corresponding reference.

TABLE 1

| Marker | Oligonucleotide Primer Sequence* | | Ref. |
|---|---|---|---|
| HXB** | ATAGCCAAAGAGAGGTGCCC | SEQ ID NO: 1 | |
| | AGAGCCCTTCTGTCTTTTCC | SEQ ID NO. 2 | 1 |
| D9S127** | CCCTCAAAATTGCTGTCTAT | SEQ ID NO: 3 | |
| | AGATTGATTGATACAAGGATTTG | SEQ ID NO: 4 | 2 |

TABLE 1-continued

| Marker | Oligonucleotide Primer Sequence* | | Ref. |
|---|---|---|---|
| D9S58** | CCTGAGTAGCCGGGACTATA | SEQ ID NO: 5 | |
| | TAGGCAACACATCAAGATCCT | SEQ ID NO: 6 | 3 |
| D9S59** | AAGGGAATTCATCCCCTGCT | SEQ ID NO: 7 | |
| | TTACACTATACCAAGACTCC | SEQ ID NO: 8 | 3 |
| ASS | GGTTGGCCTAAGAAAACCAT | SEQ ID NO: 9 | |
| | TGGGGAGCTATAAAAATGAC | SEQ ID NO: 10 | 3 |
| D9S66 | CAGACCAGGAATGCATGAAG | SEQ ID NO: 11 | |
| | CACGGGCACACATGTATGC | SEQ ID NO: 12 | 3 |
| D9S15 | TAAAGATTGGGAGTCAAGTA | SEQ ID NO: 13 | |
| | TTCACTTGATGGTGGTAATC | SEQ ID NO1 14 | 3 |
| D9S53** | GCTGCATACTTTAAACTAGC | SEQ ID NO: 15 | |
| | GGAATATGTTTTTATTAGCTTG | SEQ ID NO: 16 | 4 |
| D9S105** | GATCATATTGCTTACAACCC | SEQ ID NO: 17 | |
| | ACTTACTCATTAAATCTAGGG | SEQ ID NO: 18 | 4 |
| D9S109** | GCACAGGCTGCAATATAGAC | SEQ ID NO: 19 | |
| | TTTACTGTATAAAAACTGAAGCTAATA | SEQ ID NO: 20 | 5 |
| D9S106** | ATTGTGTTGAAATTTGACCCCT | SEQ ID NO: 21 | |
| | CCAGGCTTATTTCCACACCT | SEQ ID NO: 22 | 4 |
| ABL | TTTACACCTTCACCCAGAGA | SEQ ID NO: 23 | |
| | GGCTGTGTTCAGTTAAACGT | SEQ ID NO: 24 | 3 |
| GSN** | CAGCCAGCTTTGGAGACAAC | SEQ ID NO: 25 | |
| | TCGCAAGCATATGACTGTAA | SEQ ID NO: 26 | 6 |

*Oligonucleotide primer sequences are listed 5' to 3'.
** Markers linked to the familial dysautonomia gene.
1 Ozelius, L. et al., Human Mol. Genet. 1992; 1:141.
2 Lyall, J. E. W., et al., Nucl. Acids Res. 1992; 20:925.
3 Kwiatkowski, D. J., et al. Genomics 1992; 12:229–240.
Wilkie, P. J., et al., Genomics 1992; 12:604–609.
5 Furlong, R. A., et al., Nucl. Acids Res. 1992; 20:925.
6 Kwiatkowski, D. J., et al. Nucl. Acids Res. 1991; 19:967.

Based on the linkage results obtained with HKB, GT polymorphism analysis of chromosome 9 was performed using a panel of markers (See, Table 1) recently characterized in Kwiatkowski, D. J., et al., *Genomics* 1992; 12:229–240 (incorporated by reference); Lyall, J. E. W., et al., *Nucl. Acid Res.* 1992; 20(4):925 (incorporated by reference); Ozelius, L., et al., *Hum. Mol. Genet.* 1992; 1:141 (incorporated by reference); Wilkie, P. J., et al., *Genomics* 1992; 12:604–609 (incorporated by reference); Furlong, R.A. et al., *Nucl. Acids. Res.* 1992; 10:925 (incorporated by reference); Kwiatkowski, D. J. et al. *Nucl. Acids Res.* 1991; 19:967 (incorporated by reference) and D9S29 regular polymorphism (Williamson, R., et al., *Cytogenet. Cell Genet.* 1991; 58:1190–1833 (incorporated by reference)). Flanking markers on both sides of HXB were tested. Markers that were located closer to the centromere than HXB (e.g., D9S59, D9S58, D9S105, D9S127) gave higher lod scores, while those that were closer to the end (telomere) of the long arm (e.g., ASS) gave lower lod scores. See, Table 2.

The highest lod score was found with D9S58 (Kwiatkowski, et al., Genomics, supra) which has no recombinations between the marker and the disease status in all 26 familial dysautonomia families tested, and gave a lod score of 21.1 at zero distance. That means that D9S58 is located genetically at the same place as the familial dysautonomia gene with a ratio of $1:10^{21.1}$ in favor of linkage, while a ratio of $1:10^3$ is sufficient to prove linkage, and the maximal lod score possibly available with the 26 FD families is about 23.5 ($1:10^{23.5}$ in favor of linkage). All other markers that were typed, gave lower lod scores than D9S58, and all of them also show recombination events between the marker and the familial dysautonomia gene in some of the families. The current lod scores on chromosome 9 markers that show some linkage to the familial dysautonomia gene are summarized in FIG. 2 and Table 2. Two flanking markers that are close to D9S58 are D9S59 (telomeric) and D9S127 (centromeric to D9S58). The closest flanking markers of those analyzed are D9S53 and D9S105. These markers were mapped genetically on both sides of D9S58 on large pedigrees, at distances of 4 cM for D9S59 and about 15 cM for D9S127, and were mapped physically to the same chromosomal region as D9S58. D9S58 was mapped to a chromosomal band q31 (Kwiatkowski, et al., *Genomics,* supra); D9S127 was mapped to the same band (Lyall, et al., *Nucl. Acid Res.*, supra), and D9S59 to q31 or q32, (Kwiatkowski, et al., *Genomics*, supra) (FIG. 1).

Thus, genetic and physical data help to map the dysautonomia gene to chromosome 9q31, at the telomeric end of the band, and to a genetic region of about 20 cM around D9S58, that correlates to about 20 million nucleotides. Markers D9S53 and D9S105 further restrict the location of the FD gene to within 10 cM, i.e., 10 million nucleotides, around DS958. Although D9S58 shows complete cosegregation with the familial dysautonomia gene in all dysautonomia families that were checked, it is not possible at this stage of research to claim that D9S58 is located on top of the gene. More markers flanking D9S58 at smaller genetic distances need to be found and tested in order to locate the familial dysautonomia gene in a region small enough that will provide higher quality genetic tests for familial dysautonomia families (a region of 1–5 million nucleotides) and to specifically find the mutated gene. Narrowing down the region in which the gene is located will lead to identifying/cloning of the familial dysautonomia gene as well as sequencing thereof. Further genetic analysis employing, for example, new polymorphisms flanking D9S58 as well as the use of cosmids, YAC (yeast artificial chromosomes) clones or mixtures thereof, can be employed in the narrowing down process and techniques such as PFGE (pulsed field gel electrophoresis) or fingerprinting by Alu PCR. The next step in narrowing down will include cloning of the chromosomal region 9q31 including proximal and distal markers in a contig formed by overlapping cosmids. Subsequent subcloning in cosmids, plasmids or phages will generate additional probes for more detailed mapping.

The next step of cloning the gene will involve exon trapping, screening of cDNA libraries, Northern blots or rtPCR (reverse transcriptase PCR) of autopsy tissues from affected and unaffected individuals, direct sequencing of exons or testing exons by SSCP (single strand conformation polymorphism), RNase protection or chemical cleavage, or any other state-of-art technique.

Further localization of the FD gene to chromosome 9 was obtained as follows:

LINKAGE OF FD TO CHROMOSOME 9

Twenty-six families useful for linkage analysis were collected (FIG. 1). The first marker locus that showed a significant positive lod score was MXB (FIG. 3) in 9q32-q33 (z-9.0 at θ-0.04) (Table 2). Fourteen additional chromosome 9 markers, 9 mapping proximal to HXB and 5 mapping distal to HXB, were also tested (Table 2).

TABLE 2

PAIRWISE LOD SCORES OF CHROMOSOME 9 MARKERS WITH FD

| | RECOMBINATION FRACTION (Θ) | | | | | | | | |
|---|---|---|---|---|---|---|---|---|---|
| Marker | 0.00 | 0.01 | 0.05 | 0.10 | 0.20 | 0.30 | 0.40 | z | Θ |
| D9S15 | −∞ | −16.5 | −5.5 | −1.8 | 0.5 | 0.8 | 0.4 | 0.8 | 0.27 |
| D9S29 | −∞ | 3.8 | 5.5 | 5.3 | 3.8 | 2.1 | 0.6 | 5.6 | 0.06 |
| D9S109 | −∞ | 3.7 | 5.9 | 5.8 | 4.1 | 2.2 | 0.6 | 6.0 | 0.07 |
| D9S127 | −∞ | 6.6 | 8.0 | 7.3 | 5.0 | 2.6 | 0.7 | 8.0 | 0.05 |
| D9S53 | −∞ | 10.4 | 10.8 | 9.5 | 6.3 | 3.2 | 0.9 | 11.0 | 0.03 |
| D9S58 | 21.1 | 20.6 | 18.3 | 15.5 | 9.9 | 5.0 | 1.5 | 21.1 | 0.00 |
| D9S105 | −∞ | 13.8 | 12.8 | 11.0 | 7.2 | 3.7 | 1.1 | 13.8 | 0.01 |
| D9S59 | −∞ | 6.7 | 8.5 | 8.0 | 5.6 | 2.9 | 0.9 | 8.5 | 0.05 |
| D9S106 | −∞ | 10.1 | 10.5 | 9.4 | 6.3 | 3.3 | 0.9 | 10.7 | 0.03 |
| HXB | −∞ | 8.4 | 9.0 | 8.0 | 5.4 | 2.7 | 0.8 | 9.0 | 0.04 |
| GSN | −∞ | 2.4 | 6.0 | 6.4 | 4.8 | 2.6 | 0.8 | 6.5 | 0.08 |
| ABL | −∞ | −7.9 | −2.0 | −0.1 | 0.7 | 0.5 | 0.1 | 0.7 | 0.21 |
| ASS | −∞ | −14.9 | −5.0 | −1.6 | 0.4 | 0.6 | 0.2 | 0.6 | 0.26 |
| D9S66 | −∞ | −17.6 | −6.3 | −2.4 | 0.1 | 0.4 | 0.2 | 0.5 | 0.29 |
| D9S7 | −∞ | −6.7 | −2.8 | −1.4 | −0.4 | −0.1 | −0.0 | 0.0 | 0.50 |

Restriction fragment length polymorphisms were used for D9S29 and D9S7, while the remaining loci were typed using SSR polymorphisms. ASS was genotyped for both an RFLP and an SSR, and the results were haplotyped. Ten of the 15 markers tested detected significant linkage with FD although only D9S58 showed no recombination events with the disease gene. These DNA markers all map to 9q22.3-q33 (FIG. 3).

DEFINITION OF FLANKING MARKERS

D9S58, which showed complete cosegregation with FD, was heterozygous in 59 of the 62 parents of affected children shown in FIG. 1. the 1-lod unit confidence interval for the separation between FD and D9S58 is 1.8 cM. For the purpose of prenatal diagnosis, however, use of a single marker is prone to potential error occasioned by rare crossover events with the disease gene. Thus, close flanking markers on either side of the FD gene are required to maximize the informativeness and accuracy of prenatal or carrier testing.

To define flanking loci, the phase of selected linked markers was determined in the FD families. The order of these loci as determined by combining data from the CEPH and Venezuelan reference pedigrees is: cen-(D9S109, D9S127)-D9S53-D9S58-D9S105-D9S59-HXB-tel (FIG. 3). Recombination events in the FD families confirm this order and suggest that D9S109 maps proximal to D9S127. Similarly, markers that did not map with significant odds in the reference pedigree data could be positioned tentatively as follows: D9S29 proximal to D9S109 and D9S106 within the interval D9S59-HXB. FIGS. 4A and 4B shows examples of recombination events detected within the FD pedigrees. In FIG. 4A, recombination was detected between D9S53 and D9S105, with FD segregating with the telomeric markers. Unfortunately, in this instance the mother was homozygous at D9S58 limiting the assignment of FD to a position distal to D9S53. FIG. 4B displays two additional simple crossovers that place the FD gene proximal to D9S105 and distal to D9S53, respectively. These, and additional crossovers (not shown) are consistent with D9S53 and D9S105 being the closest flanking markers.

To provide a statistical basis supporting the definition of flanking markers, we performed multipoint linkage analysis. FD was analyzed relative to four firmly mapped marker loci: D9SS3, D9S58, D9S105 and D9S59 (FIG. 5). The genetic distances between the markers were calculated from the Venezuelan references pedigree. (Tanzi, R. E. et al., *Genomics* 1988; 3:129–136). This analysis firmly positioned FD coincident with D9S58, between D9S53 and D9S105. A localization within this interval was favored by more than 105:1 over any other interval, confirming D9S53 and D9S105 as flanking markers for genetic diagnosis.

LINKAGE DISEQUILIBRIUM WITH FD

The restriction of FD to individuals of Ashkenazi Jewish ancestry suggests the possibility of a founder effect in which most or all affected alleles share a common origin. Consequently, we examined the closely linked markers for evidence of allele association. Marker genotypes were obtained for 353 different FD chromosomes from the 26 linkage families and 148 families with single affected individuals. Four marker loci, D9S58, D9S59, D9S105 and D9S106, yielded $X^2$ values significant at p<0.01. The allele association with FD at D9S58 and D9S105 was particularly striking (Table 3).

TABLE 3

LINKAGE DISEQUILIBRIUM OF FD WITH D9S58 AND D9S105

| | | NUMBER OF CHROMOSOMES | | |
|---|---|---|---|---|
| MARKER ALLELE | PCR PRODUCT SIZE (bp) | CONTROL OBSERVED | FD EXPECTED | FD OBSERVED |
| D9S58 | | | | |
| 1 | 151 | 1 | 1 | 0 |
| 2 | 149 | 1 | 1 | 0 |

TABLE 3-continued

LINKAGE DISEQUILIBRIUM OF FD WITH D9S58 AND D9S105

| | | NUMBER OF CHROMOSOMES | | |
|---|---|---|---|---|
| MARKER ALLELE | PCR PRODUCT SIZE (bp) | CONTROL OBSERVED | FD EXPECTED | FD OBSERVED |
| 3 | 147 | 12 | 16 | 1 |
| 4 | 145 | 5 | 7 | 0 |
| 5 | 143 | 3 | 4 | 4 |
| 6 | 141 | 3 | 4 | 0 |
| 7 | 139 | 10 | 14 | 2 |
| 8 | 137 | 23 | 31 | 4 |
| 9 | 135 | 22 | 30 | 10 |
| 10 | 133 | 6 | 8 | 1 |
| 11 | 131 | 16 | 22 | 3 |
| 12 | 129 | 20 | 27 | 9 |
| 13 | 127 | 36 | 49 | 37 |
| 14 | 125 | 16 | 22 | 3 |
| 15 | 123 | 18 | 24 | 2 |
| 16 | 121 | 18 | 24 | 14 |
| 17 | 119 | 2 | 3 | 1 |
| 18 | 117 | 14 | 19 | 256 |
| 19 | 115 | 16 | 22 | 2 |
| 20 | 113 | 15 | 20 | 2 |
| 21 | 105 | 2 | 3 | 1 |
| 22 | 101 | 1 | 1 | 1 |
| | | 260 | 353 | 353 |
| | | $X^2 = 3142$ 15 D.F.* $P < 0.0001$ | | |
| D9S105 | | | | |
| 1 | 203 | 6 | 9 | 4 |
| 2 | 201 | 13 | 19 | 12 |
| 3 | 199 | 19 | 27 | 18 |
| 4 | 197 | 34 | 49 | 20 |
| 5 | 195 | 29 | 42 | 21 |
| 6 | 193 | 13 | 19 | 9 |
| 7 | 191 | 24 | 35 | 37 |
| 8 | 189 | 64 | 93 | 186 |
| 9 | 187 | 11 | 16 | 4 |
| 10 | 183 | 2 | 3 | 0 |
| | | 215 | 311 | 311 |
| | | $X^2 = 147$ 8 D.F.* $P < 0.0001$ | | |

*For D9S58 and D9S105 classes 1, 2, 5, 6, 17, 21 and 22 and classes 1 and 10, respectively, were clustered.

D9S58 displayed 22 alleles in a collection of 260 control chromosomes from the Ashkenazi Jewish population (Table 3). Eighteen of these alleles were seen on FD chromosomes, but the "18" allele (117 bp) was strikingly overrepresented. Of the 353 FD chromosomes available, 256 or 73% displayed an "8" allele for D9S58. This compares with a frequency of 5% (14 of 260) in the control Ashkenazi Jewish population. The allele association with FD was highly significant ($X^2=3142$, 15 d.f. (based on pooling classes with expected values less than 5), p<0.0001).

D9S105, located about 3 cM from D9S58, also displayed significant linkage disequilibrium with FD ($X^2=147$, 8 d.f., p<0.0001) . D9S105 possessed 10 alleles in the control population (Table 3). Allele "8" (189 bp), the most common allele in the control population (30%) was overrepresented in FD (60%).

As expected, the most frequent haplotype of D9S58 and D9S105 on FD chromosomes was "18.8" (54%). This haplotype was rare in control Ashkenazi Jews, representing just 2.5% of control chromosomes. Since the carrier frequency for FD is estimated at 3.3%, many of the "18,8" chromosomes present in the normal population may reflect FD chromosomes present in undetected carriers.

$X^2$ values for D9S59 and D9S106 were 18.1 (4 d.f.; p<0.005) and 17.3 (6 d.f.; p<0.01), respectively. The next markers proximal and distal (FIG. 3), D9S53 and HXB, showed no allele association with FD (data not shown).

ADDITIONAL MARKERS LINKED WITH THE FAMILIAL DYSAUTONOMIA GENE

Additional markers linked to familial dysautonomia gene have been identified while constructing a physical map of the familial dysautonomia gene candidate region. Cosmids were screened for the presence of repetitive DNA stretches (di, tri, tetranucleotide respeats). When a cosmid is positive on hybridization with synthetic oligonucleotides, the cosmid is subcloned into plasmids. Plasmids positive for repeat sequences are sequenced and PCR primers developed or designed to amplify the repetitive stretch identified. The markers were tested for the presence of polymorphism in a panel of control DNAs. D9S309 and D9S310 are two polymorphisms or markers identified in the candidate region for the familial dysautonomia gene by this method. (Slaugenhaupt, et al. (Povey, etal., eds) "Report on the Third International Workshop on Chromosome 9" *Ann. Hum. Genet.* (1994) 58: 177–250). D9S310 is estimated to be about 0.5 cM proximal to D9S58 and D9S309 is also proximal to D9S58 but there is no measurable genetic distance between the two markers.

Therefore yet another embodiment of this invention relates to nucleic acid sequences encoding oligonucleotides useful for detecting markers or polymorphisms linked to the familial dysautonomia gene. In particular this embodiment of the invention relates to oligonucleotides encoding flanking regions of repeat sequences which are used as primers for the polymerase chain reaction (PCR). Amplication of DNA with these primers allows for the detection of the polymorphisms D9S309 and D9S310. Such oligonucleotides may be about 15 to about 40 bases pairs in length, preferably about 17 to about 25 base pairs in length. In a preferred embodiment the oligonucleotide primers used are 5'- GCCTGGGCAAACAGAGAC-3' SEQ ID NO:27, 5'-GCAACTTATTGTTTAACCTG-3' SEQ ID NO:28 for the D9S310 polymorphism and 5'-TAGAGCTCTACCCCCCAAC-3', 5'-TGAACAGCTATATATGCCATCC-3' for the D9S309 polymorphism. It will be understood by one of skill in the art that variations in the D9S309 and the D9S310 oligonucleotide primers may be made but still result in nucleic acid sequences capable of amplifying those sequences. These oligonucleotide primers may be used in the methods described herein for detecting the presence in a subject of the D9S309 and D9S310 polymorphisms which are linked to the FD gene.

Two additional markers designated D9S172 and D9S174 were tested and demonstrated to be linked to the familial dysautonomia gene. D9S174 is approximately 2 cM distal to D9S58 and D9S172 is estimated to be about 3–4 cM proximal to D9S58. The oligonucleotide primer sequences encoding the flanking regions of the D9S172 and D9S174 polymorphisms are as follows: D9S172: 5'-AACTACAGTGTTCAGTGTGGTG-3' SEQ ID NO:31 , 5'- ATGGGAATGAGTAGCAAACA-3' SEQ ID NO:32 and D9S174: 5'- TCCAAAGTTCCCCAGGTG-3' SEQ ID NO:33, 5'-GTGTTTAATGACCCTTGTGGCTAC-3' SEQ ID NO:34 (Weissenbach, T., et al. (1992) *Nature* 359:794–801). The location of the FD gene can now be further restricted by markers D9S172 and D9S105 to within 6 cM, i.e. 6 million nucleotides around DS958.

Flanking markers on both sides of the familial dysautonomia gene combined with D9S58, or a number of well-positioned markers that cover the chromosomal region (q31)

carrying the disease gene, can give a high probability of affected or non-affected chromosomes in the range of 80–90% accuracy, depending on the informativeness of the markers used and their distance from the disease gene. Using the current markers linked to the familial dysautonomia gene, or preferably closer flanking markers when they are identified (using the above methods), a genetic test for families with familial dysautonomia-affected member is provided for both prenatal diagnosis and carrier test in healthy siblings. Subsequent delineation of even more closely linked markers which may show strong disequilibrium with the disorder, or identification of the defective gene, could also allow screening of the entire at-risk population to identify carriers, and potentially reduce the incidence of new cases of familial dysautonomia. Such closer markers, for example, D9S53, D9S105, D9S310, D9S309, D9S174 and D9S172 have now been identified and further map the location of the FD gene in the chromosome region 9q31-q33.

The method lends itself readily to the formulation of kits which can be utilized in diagnosis. Such a kit would comprise a carrier being compartmentalized to receive in close confinement one or more containers wherein a first container may contain DNA containing coding sequences which may be used to identify a given polymorphism, e.g. an SSR. A second container may contain a different set of sequences coding for a second SSR, and so on. Other containers may contain reagents useful in the detection of the labelled probes, such as enzyme substrates. Still other containers may contain restriction enzymes, buffers, and the like.

It will be obvious to those skilled in the art to which the invention pertains, that various changes and modifications may be made without departing from the scope of the invention defined by the claims.

We claim:

1. A method for detecting the presence in a subject of a polymorphism linked to a gene associated with familial dysautonomia which comprises:

analyzing human chromosome 9 of the subject and detecting the presence of a polymorphism located between D9S53 and D9S105 inclusive and linked to the gene associated with familial dysautonomia wherein the presence of the polymorphism is indicative of carriers of a gene associated with familial dysautonomia.

2. The method according to claim 1, wherein the polymorphism is selected from the group consisting of D9S53, D9S310, D9S309, D9S172 and D9S174.

3. A method for detecting the presence of polymorphisms linked to a gene associated with familial dysautonomia in a subject comprising detecting a maternal polymorphism linked to a gene associated with familial dysautonomia; detecting a paternal polymorphism linked to a gene associated with familial dysautonomia; typing the subject to determine the maternal polymorphism and paternal polymorphism; linking the distribution of the maternal polymorphism and paternal polymorphism with familial dysautonomia; and determining if the subject has the polymorphism located on the long arm human chromosome 9 between D9S53 and D9S105 inclusive linked with a gene associated with familial dysautonomia.

4. The method according to claim 1 wherein the analysis includes amplifying the polymorphism.

5. The method according to claim 1 wherein the polymorphism is detected by autoradiography.

6. The method according to claim 1 wherein the analysis includes comparison of the polymorphism of the subject to the polymorphism of each parent of the subject which are unaffected by familial dysautonomia disease and a family member affected by familial dysautonomia disease.

7. A method for detecting the presence of a polymorphism linked to a gene associated with familial dysautonomia in a subject comprising typing blood relatives of a subject for a polymorphism located on the long arm of human chromosome 9 between D9S53 and D9S105 inclusive linked with a gene associated with the familial dysautonomia; and analyzing DNA from the subject for the presence of the polymorphism.

8. A nucleic acid primer for detecting the D9S310 polymorphism associated with the familial dysautonomia gene in an individual, said primer having a nucleic acid sequence of 5'-GCCTGGGCAAA-CAGAGAC-3' (SEQ ID NO:27) or 5'-GCAACTTATTGTTTAACCTG-3' (SEQ ID NO:28).

9. A nucleic acid primer for detecting the D9S309 polymorphism associated with the familial dysautonomia gene in an individual, said primer having a nucleic acid sequence of 5'-TAGAGCTCTAC-CCCCAAC-3' (SEQ ID NO:29) or 5'-TGAACAGCTATATATGCCATCC-3' (SEQ ID NO:30).

* * * * *

```
                      SEQUENCE LISTING (1) GENERAL INFORMATION:

(iii) NUMBER OF SEQUENCES:  34

(2) INFORMATION FOR SEQ ID NO: 1:

(i) SEQUENCE CHARACTERISTICS:
        (A) LENGTH:  20
        (B) TYPE:  NUCLEIC ACID
        (C) STRANDEDNESS: SINGLE
        (D) TOPOLOGY:  UNKNOWN (ii) MOLECULE TYPE: OLIGONUCLEOTIDE (iii) HYPOTHETICAL: No (ix) FEATURE:
        (A) NAME/KEY: PRIMER SEQUENCE OF HXB LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: OZELIUS, L; SCHUBACK, DE;
            STEFANSSON, K; SLAUGENHAUPT, S;
            GUSELLA, JF; BREAKEFIELD, XO
        (B) TITLE: DINUCLEOTIDE REPEAT POLYMORPHISM
            FOR THE HEXABRACHION GENE (HXB) ON
            CHROMOSOME 9q32-34
        (C) JOURNAL: HUMAN MOLECULAR GENETICS
        (D) VOLUME: 1
        (E) ISSUE: 2
        (F) PAGES: 141
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 1:

ATAGCCAAAG AGAGGTGCCC                                               20

(2) INFORMATION FOR SEQ ID NO: 2:

(i) SEQUENCE CHARACTERISTICS:
        (A) LENGTH:  20
        (B) TYPE:  NUCLEIC ACID
        (C) STRANDEDNESS: SINGLE
        (D) TOPOLOGY:  UNKNOWN (ii) MOLECULE TYPE: OLIGONUCLEOTIDE
```

(iii) HYPOTHETICAL: No (ix) FEATURE:
              (A) NAME/KEY: PRIMER SEQUENCE OF HXB LOCUS
              (B) LOCATION: CHROMOSOME 9
              (C) IDENTIFICATION METHOD:
              (D) OTHER INFORMATION:

(x) PUBLICATION INFORMATION:
              (A) AUTHORS: OZELIUS, L; SCHUBACK, DE;
                   STEFANSSON, K; SLAUGENHAUPT, S;
                   GUSELLA, JF; BREAKEFIELD, XO
              (B) TITLE: DINUCLEOTIDE REPEAT POLYMORPHISM FOR
                   THE HEXABRACHION GENE (HXB) ON CHROMOSOME
                   9q32-34
              (C) JOURNAL: HUMAN MOLECULAR GENETICS
              (D) VOLUME: 1
              (E) ISSUE: 2
              (F) PAGES: 141
              (G) DATE: 1992
              (H) DOCUMENT NUMBER:
              (I) FILING DATE:
              (J) PUBLICATION DATE:
              (K) RELEVANT RESIDUES IN SEQ ID NO:

(xi) SEQUENCE DESCRIPTION: SEQ ID NO: 2:

AGAGCCCTTC TGTCTTTTCC                                              20

(2) INFORMATION FOR SEQ ID NO: 3:

(i) SEQUENCE CHARACTERISTICS:
              (A) LENGTH:  20
              (B) TYPE:  NUCLEIC ACID
              (C) STRANDEDNESS: SINGLE
              (D) TOPOLOGY:  UNKNOWN (ii) MOLECULE TYPE: OLIGONUCLEOTIDE (iii) HYPOTHETICAL: No (ix) FEATURE:
              (A) NAME/KEY: PRIMER SEQUENCE OF D9S127 LOCUS
              (B) LOCATION:  CHROMOSOME 9
              (C) IDENTIFICATION METHOD:
              (D) OTHER INFORMATION:

(x) PUBLICATION INFORMATION:
              (A) AUTHORS: LYALL, JEW; FURLONG, RA;
                   YUILLE, MAR; GOUDIE, DR; LEVERSHA, MA;
                   AFFARA, NA; FERGUSON-SMITH, MA
              (B) TITLE: A DINUCLEOTIDE REPEAT POLYMORPHISM
                   AT THE D9S127 LOCUS
              (C) JOURNAL: NUCLEIC ACIDS RESEARCH
              (D) VOLUME:20
              (E) ISSUE:4
              (F) PAGES: 925
              (G) DATE: 1992
              (H) DOCUMENT NUMBER:
              (I) FILING DATE:
              (J) PUBLICATION DATE:
              (K) RELEVANT RESIDUES IN SEQ ID NO:

(xi) SEQUENCE DESCRIPTION: SEQ ID NO: 3:

CCCTCAAAAT TGCTGTCTAT                                              20

(2) INFORMATION FOR SEQ ID NO: 4:

(i) SEQUENCE CHARACTERISTICS:
              (A) LENGTH:  23
              (B) TYPE:  NUCLEIC ACID
              (C) STRANDEDNESS: SINGLE
              (D) TOPOLOGY:  UNKNOWN (ii) MOLECULE TYPE: OLIGONUCLEOTIDE (iii) HYPOTHETICAL: No (ix) FEATURE:
            (A) NAME/KEY: PRIMER SEQUENCE OF D9S127 LOCUS
            (B) LOCATION: CHROMOSOME 9
            (C) IDENTIFICATION METHOD:
            (D) OTHER INFORMATION:

(x) PUBLICATION INFORMATION:
            (A) AUTHORS: LYALL, JEW; FURLONG, RA;
                YUILLE, MAR; GOUDIE, DR; LEVERSHA, MA;
                AFFARA, NA; FERGUSON-SMITH, MA
            (B) TITLE: A DINUCLEOTIDE REPEAT POLYMORPHISM
                AT THE D9S127 LOCUS
            (C) JOURNAL: NUCLEIC ACIDS RESEARCH
            (D) VOLUME:20
            (E) ISSUE:4
            (F) PAGES: 925
            (G) DATE: 1992
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 4:

AGATTGATTG ATACAAGGAT TTG                                                    23

(2) INFORMATION FOR SEQ ID NO: 5:

(i) SEQUENCE CHARACTERISTICS:
            (A) LENGTH:  20
            (B) TYPE:  NUCLEIC ACID
            (C) STRANDEDNESS: SINGLE
            (D) TOPOLOGY:  UNKNOWN (ii) MOLECULE TYPE: OLIGONUCLEOTIDE (iii) HYPOTHETICAL: No (ix) FEATURE:
            (A) NAME/KEY:PRIMER SEQUENCE FOR D9S58 LOCUS
            (B) LOCATION: CHROMOSOME 9
            (C) IDENTIFICATION METHOD:
            (D) OTHER INFORMATION:

(x) PUBLICATION INFORMATION:
            (A) AUTHORS: KWIATKOWSKI, DAVID J;
                HENSKE, ELIZABETH P; WEIMER, KIM;
                OZELIUS, LAURIE; GUSELLA, JAMES J;
                HAINES, JONATHAN
            (B) TITLE: CONSTRUCTION OF A GT POLYMORPHISM
                MAP OF HUMAN 9Q
            (C) JOURNAL: GENOMICS
            (D) VOLUME:12
            (E) ISSUE:
            (F) PAGES: 229-240
            (G) DATE: 1992
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 5:

CCTGAGTAGC CGGGACTATA                                                        20

(2) INFORMATION FOR SEQ ID NO: 6:

(i) SEQUENCE CHARACTERISTICS:
            (A) LENGTH:  21
            (B) TYPE:  NUCLEIC ACID
            (C) STRANDEDNESS: SINGLE
            (D) TOPOLOGY:  UNKNOWN (ii) MOLECULE TYPE: OLIGONUCLEOTIDE (iii) HYPOTHETICAL: No

```
        (ix) FEATURE:
              (A) NAME/KEY: PRIMER SEQUENCE OF D9S58 LOCUS
              (B) LOCATION: CHROMOSOME 9
              (C) IDENTIFICATION METHOD:
              (D) OTHER INFORMATION:

(x) PUBLICATION INFORMATION:
              (A) AUTHORS: KWIATKOWSKI, DAVID J;
                  HENSKE, ELIZABETH P; WEIMER, KIM;
                  OZELIUS, LAURIE; GUSELLA, JAMES J;
                  HAINES, JONATHAN
              (B) TITLE: CONSTRUCTION OF A GT POLYMORPHISM
                  MAP OF HUMAN 9Q
              (C) JOURNAL: GENOMICS
              (D) VOLUME:12
              (E) ISSUE:
              (F) PAGES: 229-240
              (G) DATE: 1992
              (H) DOCUMENT NUMBER:
              (I) FILING DATE:
              (J) PUBLICATION DATE:
              (K) RELEVANT RESIDUES IN SEQ ID NO:

(xi) SEQUENCE DESCRIPTION: SEQ ID NO: 6:

TAGGCAACAC ATCAAGATCC T                                               21

(2) INFORMATION FOR SEQ ID NO: 7:

(i) SEQUENCE CHARACTERISTICS:
              (A) LENGTH:  20
              (B) TYPE: NUCLEIC ACID
              (C) STRANDEDNESS: SINGLE
              (D) TOPOLOGY:  UNKNOWN (ii) MOLECULE TYPE: OLIGONUCLEOTIDE (iii) HYPOTHETICAL: No (ix) FEATURE:
              (A) NAME/KEY: PRIMER SEQUENCE OF D9S59 LOCUS
              (B) LOCATION: CHROMOSOME 9
              (C) IDENTIFICATION METHOD:
              (D) OTHER INFORMATION:

(x) PUBLICATION INFORMATION:
              (A) AUTHORS: KWIATKOWSKI, DAVID J;
                  HENSKE, ELIZABETH P; WEIMER, KIM;
                  OZELIUS, LAURIE; GUSELLA, JAMES J;
                  HAINES, JONATHAN
              (B) TITLE: CONSTRUCTION OF A GT POLYMORPHISM
                  MAP OF HUMAN 9Q
              (C) JOURNAL: GENOMICS
              (D) VOLUME:12
              (E) ISSUE:
              (F) PAGES: 229-240
              (G) DATE: 1992
              (H) DOCUMENT NUMBER:
              (I) FILING DATE:
              (J) PUBLICATION DATE:
              (K) RELEVANT RESIDUES IN SEQ ID NO:

(xi) SEQUENCE DESCRIPTION: SEQ ID NO: 7:

AAGGGAATTC ATCCCCTGCT                                                 20

(2) INFORMATION FOR SEQ ID NO: 8:

(i) SEQUENCE CHARACTERISTICS:
              (A) LENGTH:  20
              (B) TYPE:  NUCLEIC ACID
              (C) STRANDEDNESS: SINGLE
              (D) TOPOLOGY:  UNKNOWN (ii) MOLECULE TYPE: OLIGONUCLEOTIDE (iii) HYPOTHETICAL: No
```

(ix) FEATURE:
        (A) NAME/KEY: PRIMER SEQUENCE OF D9S59 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: KWIATKOWSKI, DAVID J;
            HENSKE, ELIZABETH P; KIM; OZELIUS, LAURIE;
            GUSELLA, JAMES J; HAINES, JONATHAN
        (B) TITLE: CONSTRUCTION OF A GT POLYMORPHISM
            MAP OF HUMAN 9Q
        (C) JOURNAL: GENOMICS
        (D) VOLUME:12
        (E) ISSUE:
        (F) PAGES: 229-240
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 8:

TTACACTATA CCAAGACTCC                                                20

(2) INFORMATION FOR SEQ ID NO: 9:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: UNKNOWN (ii) MOLECULE TYPE: OLIGONUCLEOTIDE (iii) HYPOTHETICAL: No (ix) FEATURE:
        (A) NAME/KEY: PRIMER SEQUENCE OF ASS LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: KWIATKOWSKI, DAVID J;
            HENSKE, ELIZABETH P; WEIMER, KIM;
            OZELIUS, LAURIE; GUSELLA, JAMES J;
            HAINES, JONATHAN
        (B) TITLE: CONSTRUCTION OF A GT POLYMORPHISM
            MAP OF HUMAN 9Q
        (C) JOURNAL: GENOMICS
        (D) VOLUME:12
        (E) ISSUE:
        (F) PAGES: 229-240
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 9:

GGTTGGCCTA AGAAAACCAT                                                20

(2) INFORMATION FOR SEQ ID NO: 10:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: UNKNOWN (ii) MOLECULE TYPE: OLIGONUCLEOTIDE (iii) HYPOTHETICAL: No (ix) FEATURE:

(A) NAME/KEY: PRIMER SEQUENCE OF ASS LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: KWIATKOWSKI, DAVID J;
            HENSKE, ELIZABETH P; WEIMER, KIM;
            OZELIUS, LAURIE; GUSELLA, JAMES J;
            HAINES, JONATHAN
        (B) TITLE: CONSTRUCTION OF A GT POLYMORPHISM
            MAP OF HUMAN 9Q
        (C) JOURNAL: GENOMICS
        (D) VOLUME:12
        (E) ISSUE:
        (F) PAGES: 229-240
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 10:

TGGGGAGCTA TAAAAATGAC                                                     20

(2) INFORMATION FOR SEQ ID NO: 11:

(i) SEQUENCE CHARACTERISTICS:
        (A) LENGTH:  20
        (B) TYPE:  NUCLEIC ACID
        (C) STRANDEDNESS: SINGLE
        (D) TOPOLOGY:  UNKNOWN (ii) MOLECULE TYPE: OLIGONUCLEOTIDE (iii) HYPOTHETICAL: No (ix) FEATURE:
        (A) NAME/KEY: PRIMER SEQUENCE OF D9S66 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: KWIATKOWSKI, DAVID J;
            HENSKE, ELIZABETH P; WEIMER, KIM;
            OZELIUS, LAURIE; GUSELLA, JAMES J;
            HAINES, JONATHAN
        (B) TITLE: CONSTRUCTION OF A GT POLYMORPHISM
            MAP OF HUMAN 9Q
        (C) JOURNAL: GENOMICS
        (D) VOLUME:12
        (E) ISSUE:
        (F) PAGES: 229-240
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 11:

CAGACCAGGA ATGCATGAAG                                                     20

(2) INFORMATION FOR SEQ ID NO: 12:

(i) SEQUENCE CHARACTERISTICS:
        (A) LENGTH:  19
        (B) TYPE:  NUCLEIC ACID
        (C) STRANDEDNESS: SINGLE
        (D) TOPOLOGY:  UNKNOWN (ii) MOLECULE TYPE: OLIGONUCLEOTIDE (iii) HYPOTHETICAL: No (ix) FEATURE:

(A) NAME/KEY: PRIMER SEQUENCE OF D9S66 LOCUS
            (B) LOCATION: CHROMOSOME 9
            (C) IDENTIFICATION METHOD:
            (D) OTHER INFORMATION:

(x) PUBLICATION INFORMATION:
            (A) AUTHORS: KWIATKOWSKI, DAVID J;
                HENSKE, ELIZABETH P; WEIMER, KIM;
                OZELIUS, LAURIE; GUSELLA, JAMES J;
                HAINES, JONATHAN
            (B) TITLE: CONSTRUCTION OF A GT POLYMORPHISM
                MAP OF HUMAN 9Q
            (C) JOURNAL: GENOMICS
            (D) VOLUME:12
            (E) ISSUE:
            (F) PAGES: 229-240
            (G) DATE: 1992
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 12:

CACGGGCACA CATGTATGC                                                    19

(2) INFORMATION FOR SEQ ID NO: 13:

(i) SEQUENCE CHARACTERISTICS:
            (A) LENGTH:  20
            (B) TYPE:  NUCLEIC ACID
            (C) STRANDEDNESS: SINGLE
            (D) TOPOLOGY:  UNKNOWN (ii) MOLECULE TYPE: OLIGONUCLEOTIDE (iii) HYPOTHETICAL: No (ix) FEATURE:
            (A) NAME/KEY: PRIMER SEQUENCE OF D9S15 LOCUS
            (B) LOCATION: CHROMOSOME 9
            (C) IDENTIFICATION METHOD:
            (D) OTHER INFORMATION:

(x) PUBLICATION INFORMATION:
            (A) AUTHORS: KWIATKOWSKI, DAVID J;
                HENSKE, ELIZABETH P; WEIMER, KIM;
                OZELIUS, LAURIE; GUSELLA, JAMES J;
                HAINES, JONATHAN
            (B) TITLE: CONSTRUCTION OF A GT POLYMORPHISM
                MAP OF HUMAN 9Q
            (C) JOURNAL: GENOMICS
            (D) VOLUME:12
            (E) ISSUE:
            (F) PAGES: 229-240
            (G) DATE: 1992
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 13:

TAAAGATTGG GAGTCAAGTA                                                   20

(2) INFORMATION FOR SEQ ID NO: 14:

(i) SEQUENCE CHARACTERISTICS:
            (A) LENGTH:  20
            (B) TYPE:  NUCLEIC ACID
            (C) STRANDEDNESS: SINGLE
            (D) TOPOLOGY:  UNKNOWN (ii) MOLECULE TYPE: OLIGONUCLEOTIDE (iii) HYPOTHETICAL: No (ix) FEATURE:

(A) NAME/KEY: PRIMER SEQUENCE OF D9S15 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: KWIATKOWSKI, DAVID J;
            HENSKE, ELIZABETH P; WEIMER, KIM;
            OZELIUS, LAURIE; GUSELLA, JAMES J;
            HAINES, JONATHAN
        (B) TITLE: CONSTRUCTION OF A GT POLYMORPHISM
            MAP OF HUMAN 9Q
        (C) JOURNAL: GENOMICS
        (D) VOLUME:12
        (E) ISSUE:
        (F) PAGES: 229-240
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 14:

TTCACTTGAT GGTGGTAATC                                           20

(2) INFORMATION FOR SEQ ID NO: 15:

(i) SEQUENCE CHARACTERISTICS:
        (A) LENGTH:  20
        (B) TYPE:  NUCLEIC ACID
        (C) STRANDEDNESS: SINGLE
        (D) TOPOLOGY:  UNKNOWN (ii) MOLECULE TYPE: OLIGONUCLEOTIDE (iii) HYPOTHETICAL: No (ix) FEATURE:
        (A) NAME/KEY: PRIMER SEQUENCE OF D9S53 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: WILKIE, PJ; KRIZMAN, DB; WEBER; JL
        (B) TITLE: LINKAGE MAP OF HUMAN CHROMOSOME 9
            MICROSATELLITE POLYMORPHISMS
        (C) JOURNAL: GENOMICS
        (D) VOLUME: 12
        (E) ISSUE:
        (F) PAGES: 607-609
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 15:

GCTGCATACT TTAAACTAGC                                           20

(2) INFORMATION FOR SEQ ID NO: 16:

(i) SEQUENCE CHARACTERISTICS:
        (A) LENGTH:  22
        (B) TYPE:  NUCLEIC ACID
        (C) STRANDEDNESS: SINGLE
        (D) TOPOLOGY:  UNKNOWN (ii) MOLECULE TYPE: OLIGONUCLEOTIDE (iii) HYPOTHETICAL: No (ix) FEATURE:
        (A) NAME/KEY: PRIMER SEQUENCE OF D9S53 LOCUS
        (B) LOCATION: CHROMOSOME 9
        (C) IDENTIFICATION METHOD:

```
        (D) OTHER INFORMATION:

(x) PUBLICATION INFORMATION:
        (A) AUTHORS: WILKIE, PJ; KRIZMAN, DB; WEBER; JL
        (B) TITLE: LINKAGE MAP OF HUMAN CHROMOSOME 9
                MICROSATELLITE POLYMORPHISMS
        (C) JOURNAL: GENOMICS
        (D) VOLUME: 12
        (E) ISSUE:
        (F) PAGES: 607-609
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 16:

GGAATATGTT TTTATTAGCT TG                                              22

(2) INFORMATION FOR SEQ ID NO: 17:

(i) SEQUENCE CHARACTERISTICS:
        (A) LENGTH:  20
        (B) TYPE:  NUCLEIC ACID
        (C) STRANDEDNESS: SINGLE
        (D) TOPOLOGY:  UNKNOWN (ii) MOLECULE TYPE: OLIGONUCLEOTIDE (iii) HYPOTHETICAL: No (ix) FEATURE:
        (A) NAME/KEY: PRIMER SEQUENCE OF D9S105 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: WILKIE, PJ; KRIZMAN, DB; WEBER; JL
        (B) TITLE: LINKAGE MAP OF HUMAN CHROMOSOME 9
                MICROSATELLITE POLYMORPHISMS
        (C) JOURNAL: GENOMICS
        (D) VOLUME: 12
        (E) ISSUE:
        (F) PAGES: 607-609
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 17:

GATCATATTG CTTACAACCC                                                 20

(2) INFORMATION FOR SEQ ID NO: 18:

(i) SEQUENCE CHARACTERISTICS:
        (A) LENGTH:  21
        (B) TYPE:  NUCLEIC ACID
        (C) STRANDEDNESS: SINGLE
        (D) TOPOLOGY:  UNKNOWN (ii) MOLECULE TYPE: OLIGONUCLEOTIDE (iii) HYPOTHETICAL: No (ix) FEATURE:
        (A) NAME/KEY: PRIMER SEQUENCE OF D9S105 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: WILKIE, PJ; KRIZMAN, DB; WEBER; JL
        (B) TITLE: LINKAGE MAP OF HUMAN CHROMOSOME 9
                MICROSATELLITE POLYMORPHISMS
```

```
        (C) JOURNAL: GENOMICS
        (D) VOLUME: 12
        (E) ISSUE:
        (F) PAGES: 607-609
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 18:

ACTTACTCAT TAAATCTAGG G                                          21

(2) INFORMATION FOR SEQ ID NO: 19:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: UNKNOWN (ii) MOLECULE TYPE: OLIGONUCLEOTIDE (iii) HYPOTHETICAL: No (ix) FEATURE:
        (A) NAME/KEY: PRIMER SEQUENCE OF D9S109 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: FURLONG, PA; LYALL, JE; GOUDIE,
            DR; LEVERSHA, MA; AFFARA, NA; FERGUSON-
            SMITH, MA
        (B) TITLE: A DINUCLEOTIDE REPEAT POLYMORPHISM
            AT THE D9S109 LOCUS
        (C) JOURNAL: NUCLEIC ACIDS RESEARCH
        (D) VOLUME: 20
        (E) ISSUE:
        (F) PAGES: 925
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 19:

GCACAGGCTG CAATATAGAC                                            20

(2) INFORMATION FOR SEQ ID NO: 20:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: UNKNOWN (ii) MOLECULE TYPE: OLIGONUCLEOTIDE (iii) HYPOTHETICAL: No (ix) FEATURE:
        (A) NAME/KEY: PRIMER SEQUENCE OF D9S109 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: FURLONG, PA; LYALL, JE; GOUDIE,
            DR; LEVERSHA, MA; AFFARA, NA; FERGUSON-
            SMITH, MA
        (B) TITLE: A DINUCLEOTIDE REPEAT POLYMORPHISM
            AT THE D9S109 LOCUS
        (C) JOURNAL: NUCLEIC ACIDS RESEARCH
        (D) VOLUME: 20
```

```
        (E) ISSUE:
        (F) PAGES:  925
        (G) DATE:  1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 20:

TTTACTGTAT AAAAACTGAA GCTAATA                                                27

(2) INFORMATION FOR SEQ ID NO: 21:

(i) SEQUENCE CHARACTERISTICS:
        (A) LENGTH:  22
        (B) TYPE:  NUCLEIC ACID
        (C) STRANDEDNESS: SINGLE
        (D) TOPOLOGY:  UNKNOWN (ii) MOLECULE TYPE: OLIGONUCLEOTIDE (iii) HYPOTHETICAL: No (ix) FEATURE:
        (A) NAME/KEY: PRIMER SEQUENCE OF D9S106 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: WILKIE PJ; KRIZMAN, DB; WEBER; JL
        (B) TITLE: LINKAGE MAP OF HUMAN CHROMOSOME 9
            MICROSATELLITE POLYMORPHISMS
        (C) JOURNAL: GENOMICS
        (D) VOLUME: 12
        (E) ISSUE:
        (F) PAGES: 607-609
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 21:

ATTGTGTTGA AATTTGACCC CT                                                     22

(2) INFORMATION FOR SEQ ID NO: 22:

(i) SEQUENCE CHARACTERISTICS:
        (A) LENGTH:  20
        (B) TYPE:  NUCLEIC ACID
        (C) STRANDEDNESS: SINGLE
        (D) TOPOLOGY:  UNKNOWN (ii) MOLECULE TYPE: OLIGONUCLEOTIDE (iii) HYPOTHETICAL: No (ix) FEATURE:
        (A) NAME/KEY: PRIMER SEQUENCE OF D9S106 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: WILKIE, PJ; KRIZMAN, DB; WEBER; JL
        (B) TITLE: LINKAGE MAP OF HUMAN CHROMOSOME 9
            MICROSATELLITE POLYMORPHISMS
        (C) JOURNAL: GENOMICS
        (D) VOLUME: 12
        (E) ISSUE:
        (F) PAGES: 607-609
        (G) DATE: 1992
        (H) DOCUMENT NUMBER:
        (I) FILING DATE:
        (J) PUBLICATION DATE:
```

(K) RELEVANT RESIDUES IN SEQ ID NO:

(xi) SEQUENCE DESCRIPTION: SEQ ID NO: 22:

CCAGGCTTAT TTCCACACCT                                                              20

(2) INFORMATION FOR SEQ ID NO: 23:

(i) SEQUENCE CHARACTERISTICS:
         (A) LENGTH:  20
         (B) TYPE:  NUCLEIC ACID
         (C) STRANDEDNESS: SINGLE
         (D) TOPOLOGY:  UNKNOWN (ii) MOLECULE TYPE: OLIGONUCLEOTIDE (iii) HYPOTHETICAL: No (ix) FEATURE:
         (A) NAME/KEY: PRIMER SEQUENCE OF ABL LOCUS
         (B) LOCATION: CHROMOSOME 9
         (C) IDENTIFICATION METHOD:
         (D) OTHER INFORMATION:

(x) PUBLICATION INFORMATION:
         (A) AUTHORS: KWIATKOWSKI, DAVID J; HENSKE,
             ELIZABETH P; WEIMER, KIM; OZELIUS, LAURIE;
             GUSELLA, JAMES J; HAINES, JONATHAN
         (B) TITLE: CONSTRUCTION OF A GT POLYMORPHISM
             MAP OF HUMAN 9Q
         (C) JOURNAL: GENOMICS
         (D) VOLUME:12
         (E) ISSUE:
         (F) PAGES: 229-240
         (G) DATE: 1992
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO: 23:

TTTACACCTT CACCCAGAGA                                                              20

(2) INFORMATION FOR SEQ ID NO: 24:

(i) SEQUENCE CHARACTERISTICS:
         (A) LENGTH:  20
         (B) TYPE:  NUCLEIC ACID
         (C) STRANDEDNESS: SINGLE
         (D) TOPOLOGY:  UNKNOWN (ii) MOLECULE TYPE: OLIGONUCLEOTIDE (iii) HYPOTHETICAL: No (ix) FEATURE:
         (A) NAME/KEY: PRIMER SEQUENCE OF ABL LOCUS
         (B) LOCATION: CHROMOSOME 9
         (C) IDENTIFICATION METHOD:
         (D) OTHER INFORMATION:

(x) PUBLICATION INFORMATION:
         (A) AUTHORS: KWIATKOWSKI, DAVID J; HENSKE,
             ELIZABETH P; WEIMER, KIM; OZELIUS, LAURIE;
             GUSELLA, JAMES J; HAINES, JONATHAN
         (B) TITLE: CONSTRUCTION OF A GT POLYMORPHISM
             MAP OF HUMAN 9Q
         (C) JOURNAL: GENOMICS
         (D) VOLUME:12
         (E) ISSUE:
         (F) PAGES: 229-240
         (G) DATE: 1992
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO: 24:

GGCTGTGTTC AGTTAAACGT                                                    20

(2) INFORMATION FOR SEQ ID NO: 25:

(i) SEQUENCE CHARACTERISTICS:
              (A) LENGTH: 20
              (B) TYPE: NUCLEIC ACID
              (C) STRANDEDNESS: SINGLE
              (D) TOPOLOGY: UNKNOWN (ii) MOLECULE TYPE: OLIGONUCLEOTIDE (iii) HYPOTHETICAL: No (ix) FEATURE:
              (A) NAME/KEY: PRIMER SEQUENCE OF GSN LOCUS
              (B) LOCATION: CHROMOSOME 9
              (C) IDENTIFICATION METHOD:
              (D) OTHER INFORMATION:

(x) PUBLICATION INFORMATION:
              (A) AUTHORS: KWIATKOWSKI, DJ; PERMAN, S
              (B) TITLE: DINUCLEOTIDE REPEAT POLYMORPHISM AT
                    THE GSN LOCUS (9q 32-34)
              (C) JOURNAL: NUCLEIC ACIDS RESEARCH
              (D) VOLUME: 19
              (E) ISSUE:
              (F) PAGES: 967
              (G) DATE: 1991
              (H) DOCUMENT NUMBER:
              (I) FILING DATE:
              (J) PUBLICATION DATE:
              (K) RELEVANT RESIDUES IN SEQ ID NO:

(xi) SEQUENCE DESCRIPTION: SEQ ID NO: 25:

CAGCCAGCTT TGGAGACAAC                                                    20

(2) INFORMATION FOR SEQ ID NO: 26:

(i) SEQUENCE CHARACTERISTICS:
              (A) LENGTH: 20
              (B) TYPE: NUCLEIC ACID
              (C) STRANDEDNESS: SINGLE
              (D) TOPOLOGY: UNKNOWN (ii) MOLECULE TYPE: OLIGONUCLEOTIDE (iii) HYPOTHETICAL: No (ix) FEATURE:
              (A) NAME/KEY: PRIMER SEQUENCE OF GSN LOCUS
              (B) LOCATION: CHROMOSOME 9
              (C) IDENTIFICATION METHOD:
              (D) OTHER INFORMATION:

(x) PUBLICATION INFORMATION:
              (A) AUTHORS: KWIATKOWSKI, DJ; PERMAN, S
              (B) TITLE: DINUCLEOTIDE REPEAT POLYMORPHISM AT
                    THE GSN LOCUS (9q 32-34)
              (C) JOURNAL: NUCLEIC ACIDS RESEARCH
              (D) VOLUME: 19
              (E) ISSUE:
              (F) PAGES: 967
              (G) DATE: 1991
              (H) DOCUMENT NUMBER:
              (I) FILING DATE:
              (J) PUBLICATION DATE:
              (K) RELEVANT RESIDUES IN SEQ ID NO:

(xi) SEQUENCE DESCRIPTION: SEQ ID NO: 26:

TCGCAAGCAT ATGACTGTAA                                                    20

(2) INFORMATION FOR SEQ ID NO: 27:

```
            (i) SEQUENCE CHARACTERISTICS:
                (A) LENGTH: 18
                (B) TYPE:  NUCLEIC ACID
                (C) STRANDEDNESS: SINGLE
                (D) TOPOLOGY:  UNKNOWN (ii) MOLECULE TYPE: OLIGONUCLEOTIDE (iii) HYPOTHETICAL: No (ix) FEATURE:
                (A) NAME/KEY: PRIMER SEQUENCE OF D9S310 LOCUS
                (B) LOCATION: CHROMOSOME 9
                (C) IDENTIFICATION METHOD:
                (D) OTHER INFORMATION:

(xi) SEQUENCE DESCRIPTION: SEQ ID NO: 27:

GCCTGGGCAA ACAGAGAC                                                          18

(2) INFORMATION FOR SEQ ID NO: 28:

(i) SEQUENCE CHARACTERISTICS:
                (A) LENGTH: 20
                (B) TYPE:  NUCLEIC ACID
                (C) STRANDEDNESS: SINGLE
                (D) TOPOLOGY:  UNKNOWN (ii) MOLECULE TYPE: OLIGONUCLEOTIDE (iii) HYPOTHETICAL: No (ix) FEATURE:
                (A) NAME/KEY: PRIMER SEQUENCE OF D9S310 LOCUS
                (B) LOCATION: CHROMOSOME 9
                (C) IDENTIFICATION METHOD:
                (D) OTHER INFORMATION:

(xi) SEQUENCE DESCRIPTION: SEQ ID NO: 28:

GCAACTTATT GTTTAACCTG                                                        20

(2) INFORMATION FOR SEQ ID NO: 29:

(i) SEQUENCE CHARACTERISTICS:
                (A) LENGTH: 19
                (B) TYPE:  NUCLEIC ACID
                (C) STRANDEDNESS: SINGLE
                (D) TOPOLOGY:  UNKNOWN (ii) MOLECULE TYPE: OLIGONUCLEOTIDE (iii) HYPOTHETICAL: No (ix) FEATURE:
                (A) NAME/KEY: PRIMER SEQUENCE OF D9S309 LOCUS
                (B) LOCATION: CHROMOSOME 9
                (C) IDENTIFICATION METHOD:
                (D) OTHER INFORMATION:

(xi) SEQUENCE DESCRIPTION: SEQ ID NO: 29:

TAGAGCTCTA CCCCCCAAC                                                         19

(2) INFORMATION FOR SEQ ID NO: 30:

(i) SEQUENCE CHARACTERISTICS:
                (A) LENGTH: 22
                (B) TYPE:  NUCLEIC ACID
                (C) STRANDEDNESS: SINGLE
                (D) TOPOLOGY:  UNKNOWN (ii) MOLECULE TYPE: OLIGONUCLEOTIDE (iii) HYPOTHETICAL: No
```

```
    (ix) FEATURE:
         (A) NAME/KEY: PRIMER SEQUENCE OF D9S309 LOCUS
         (B) LOCATION: CHROMOSOME 9
         (C) IDENTIFICATION METHOD:
         (D) OTHER INFORMATION:

(xi) SEQUENCE DESCRIPTION: SEQ ID NO: 30:

TGAACAGCTA TATATGCCAT CC                                              22

(2) INFORMATION FOR SEQ ID NO: 31:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: UNKNOWN (ii) MOLECULE TYPE: OLIGONUCLEOTIDE (iii) HYPOTHETICAL: No (ix) FEATURE:
         (A) NAME/KEY: PRIMER SEQUENCE OF D9S172 LOCUS
         (B) LOCATION: CHROMOSOME 9
         (C) IDENTIFICATION METHOD:
         (D) OTHER INFORMATION:

(x) PUBLICATION INFORMATION:
        (A) AUTHORS: WEISSENBACH, ET AL.
        (B) TITLE: A SECOND GENERATION LINKAGE MAP OF
            THE HUMAN GENOME
        (C) JOURNAL: NATURE
        (D) VOLUME: 359
        (E) ISSUE:
        (F) PAGES: 794
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 31:

AACTACAGTG TTCAGTGTGG TG                                              22

(2) INFORMATION FOR SEQ ID NO: 32:

(i) SEQUENCE CHARACTERISTICS:
        (A) LENGTH: 20
        (B) TYPE: NUCLEIC ACID
        (C) STRANDEDNESS: SINGLE
        (D) TOPOLOGY: UNKNOWN (ii) MOLECULE TYPE: OLIGONUCLEOTIDE (iii) HYPOTHETICAL: No (ix) FEATURE:
         (A) NAME/KEY: PRIMER SEQUENCE OF D9S172 LOCUS
         (B) LOCATION: CHROMOSOME 9
         (C) IDENTIFICATION METHOD:
         (D) OTHER INFORMATION:

(x) PUBLICATION INFORMATION:
        (A) AUTHORS: WEISSENBACH, ET AL.
        (B) TITLE: A SECOND GENERATION LINKAGE MAP OF
            THE HUMAN GENOME
        (C) JOURNAL: NATURE
        (D) VOLUME: 359
        (E) ISSUE:
        (F) PAGES: 794
        (G) DATE: 1992
        (H) DOCUMENT NUMBER:
        (I) FILING DATE:
        (J) PUBLICATION DATE:
        (K) RELEVANT RESIDUES IN SEQ ID NO:
```

-continued (xi) SEQUENCE DESCRIPTION: SEQ ID NO: 32:

ATGGGAATGA GTAGCAAACA                                                    20

(2) INFORMATION FOR SEQ ID NO: 33:

(i) SEQUENCE CHARACTERISTICS:
        (A) LENGTH: 18
        (B) TYPE: NUCLEIC ACID
        (C) STRANDEDNESS: SINGLE
        (D) TOPOLOGY: UNKNOWN (ii) MOLECULE TYPE: OLIGONUCLEOTIDE (iii) HYPOTHETICAL: No (ix) FEATURE:
        (A) NAME/KEY: PRIMER SEQUENCE OF D9S174 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: WEISSENBACH, ET AL.
        (B) TITLE: A SECOND GENERATION LINKAGE MAP OF
            THE HUMAN GENOME
        (C) JOURNAL: NATURE
        (D) VOLUME: 359
        (E) ISSUE:
        (F) PAGES: 794
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 33:

TCCAAAGTTC CCCAGGTG                                                      18

(2) INFORMATION FOR SEQ ID NO: 34:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: UNKNOWN (ii) MOLECULE TYPE: OLIGONUCLEOTIDE (iii) HYPOTHETICAL: No (ix) FEATURE:
        (A) NAME/KEY: PRIMER SEQUENCE OF D9S174 LOCUS
        (B) LOCATION: CHROMOSOME 9
        (C) IDENTIFICATION METHOD:
        (D) OTHER INFORMATION:

(x) PUBLICATION INFORMATION:
        (A) AUTHORS: WEISSENBACH, ET AL.
        (B) TITLE: A SECOND GENERATION LINKAGE MAP OF
            THE HUMAN GENOME
        (C) JOURNAL: NATURE
        (D) VOLUME: 359
        (E) ISSUE:
        (F) PAGES: 794
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 34:

GTGTTTAATG ACCCTTGTGG CTAC                                               24